United States Patent [19]

Freedman et al.

[11] Patent Number: 5,434,076
[45] Date of Patent: Jul. 18, 1995

[54] TUMOR-SPECIFIC, CELL SURFACE-BINDING MONOCLONAL ANTIBODIES

[75] Inventors: Ralph S. Freedman; Constantin G. Ioannides, both of Houston; Barbara J. Tomasovic, Kingwood; Rebecca S. Patenia, Sugar Land, all of Tex.

[73] Assignee: Board of Regents, The University of Texas System, Austin, Tex.

[21] Appl. No.: 862,768

[22] PCT Filed: Dec. 18, 1990

[86] PCT No.: PCT/US90/07496

§ 371 Date: Aug. 21, 1992

§ 102(e) Date: Aug. 21, 1992

[87] PCT Pub. No.: WO91/09135

PCT Pub. Date: Jun. 27, 1991

Related U.S. Application Data

[63] Continuation-in-part of Ser. No. 452,733, Dec. 18, 1989, abandoned.

[51] Int. Cl.⁶ .......................... C12N 5/24; C12N 5/22; C07K 16/30; C07K 16/28
[52] U.S. Cl. ........................ 435/240.27; 435/70.21; 435/172.2; 530/388.15; 530/388.8; 530/388.85; 530/389.7; 530/865
[58] Field of Search ................. 424/85.8, 85.91, 86, 424/89, 174.1, 142.1; 530/388.15, 388.8, 388.85, 391.1, 389.7, 391.3, 865, 391.7; 435/70.21, 172.2, 240.27

[56] References Cited

FOREIGN PATENT DOCUMENTS 8304313 12/1983 WIPO .

OTHER PUBLICATIONS

Freedman et al., Hybridoma, vol. 10, pp. 21–33, 1991.
Klein, J. Interferon Res, vol. 7, #5, pp. 583–589, 1987 (Abstract Thereof).
Freedman et al., Gynecol. Oncol. vol. 29, pp. 337–347, 1988.
Ioannides et al., Anticancer Res, vol. 9, pp. 81–86, 1989.
Aotsuka et al., Eur. J. Clin. Oncol., vol. 24, #5, pp. 829–838, 1988.
Ahmad et al., TIB Tech, vol. 6, pp. 246–251, 1988.
Waldmann, Science, vol. 262, pp. 1657–1662, 1991.
Werner et al., Gynecol. Oncol., vol. 34, pp. 148–154, 1989.
Ostberg et al., Hybridoma, vol. 2, #4, pp. 361–367, 1983.
Goldenberg, Arch Pathol. Lab. Med., vol. 112, pp. 580–587, 1988.

*Primary Examiner*—David L. Lacey
*Assistant Examiner*—Ron Schwadron
*Attorney, Agent, or Firm*—Arnold, White & Durkee

[57] ABSTRACT

Disclosed is a process for the preparation and use of gynecological tumor diagnostic and antitumor reagents. The process involves the pre-treatment of a patient with a viral oncolysate and the establishment of stable B cell human hybridomas capable of producing human monoclonal antibodies reactive with cell surface epitopes of human gynecological tumors. At least one such surface epitope is described as is the association constant of the antibody for certain gynecological tumor cells. Also disclosed are methods for utilizing the monoclonal antibodies of the invention in diagnoses and treatment of gynecological malignancies. In addition, two particularly useful gynecological hybridoma lines are disclosed which were derived from the process of the invention.

2 Claims, 9 Drawing Sheets

TUMOR-SPECIFIC, CELL SURFACE-BINDING MONOCLONAL ANTIBODIES

This application is the national stage application of PCT U.S. Pat. No. 90/07496, which is a CIP of U.S. application 07/452,733, (now abandoned), filed Dec. 18, 1989.

The present invention relates to novel tumor diagnostic and antitumor reagents, including processes for their preparation and use. In particular aspects, the invention concerns establishment of stable human B cell hybridomas capable of producing human monoclonal antibodies reactive with surface epitopes of human gynecological tumors in a specific manner. The invention further provides for such monoclonal antibodies of known association constants. Certain of these antibodies recognize a proteinaceous surface epitope which has been characterized as a glycoprotein. The invention further relates to the use of these antibodies in the diagnosis and treatment of gynecological malignancies.

a. Monoclonal antibodies of gynecological origin.

The detection of gynecological tumors at an early stage is an essential element in the successful control of these cancers. Likewise, early treatment of these tumors can be determinative of the progression of the disease. Numerous studies have explored the use of immunological reagents for both detection and treatment of tumors including carcinomas of gynecological tissues. Generally, development in this area of cancer research has been toward increasingly refined reagents designed to attack or detect species-specific, tumor-specific, cell surface-specific regions of the diseased tissue.

Some of the earlier approaches to develop immunological reagents for the detection of cervical carcinomas involved immunizing mice with human cervical carcinoma cells. These studies demonstrated certain gains by providing monoclonal antibodies with selected specificity for cervical carcinomas (Koprowska, et al., 1986). The practical problems associated with in vivo use of foreign antibodies in humans, however, such as the induction of a human anti-mouse response when using murine monoclonal antibodies, were recognized as possible elements in the reduction of the efficacy in immunotherapy. In a number of clinical trials to date, murine monoclonal antibodies have been used to treat patients possessing solid tumors. Generally, therapeutic efficacy has been transient or absent using this approach (Houghton, et al., 1985; Oldham, et al., 1984; Sears, et al., 1982).

To overcome these problems, workers have focused on production of chimeric (human-mouse) or human-human antibodies. For instance, it was recognized that increased specificity of immunological reagents which are non-immunogenic when injected into primates or humans could be obtained by replacing mouse cell fusions with human-human fusions to produce hybridomas secreting human monoclonal antibodies. In one approach, the fusion of human lymphocytes with mouse myeloma cells was shown to be a useful procedure for human monoclonal antibody production. Hybridomas of such heteromyeloma cell lines with human cells overcomes some of the problems encountered with construction and maintenance of stable human hybrids such as low concentrations of secreted immunoglobulins and lack of suitable methods for large-scale production.

Using the human-human fusion approach, Hagiwara and Sato were able to produce a human immunoglobulin G (IgG) monoclonal antibody which reacted with autologous cervical carcinoma cells and with tumor cell lines of cervical origin. This monoclonal antibody, however, was not specific to cervical carcinoma epitopes since it reacted with other tumor cells as well, including melanomas, prostate carcinomas, colon carcinomas and hepatomas (Hagiwara & Sato, 1983). A similar approach was used by Glassy and co-workers to obtain human-human monoclonal antibodies specific to a wide range of tumor types and tissues of origin including cancer of the vulva. (Glassy, et al., 1987; Glassy and Surh, 1988). Although the studies of Hagiwara & Sato and of Glassy, et al. were successful in obtaining species-specific (human-human) monoclonal antibodies, the cell surface specificity of these antibodies was not extensively characterized.

Tumor immunotherapy is based on the concept that malignant tumor cells express unique cell surface epitopes not found in non-tumor cells. For the therapies to be most effective, cell surface distribution of the tumor antigens is crucial since initial steps of antibody-mediated mechanisms against tumors (e.g., complement dependent cytotoxicity and antibody dependent cell mediated toxicity) occur at the surface of tumor cells with exposed antigens.

For these reasons, the importance has been stressed of obtaining not only species-specific and tumor-specific antibodies but also the advantages of producing antibodies to specific antigens on the surface of a given tumor cell type. Early studies have utilized human-human monoclonal antibodies and have reported tumor specific reactions. These workers failed to indicate whether they obtained cell-surface reactivity or not. However, in some instances antibodies have been reported to "bind to" the target cell line (Handley, et al., 1983; Handley, et al., 1986; Al-Azzawi, et al., 1987).

In later studies, very large numbers of B-cell, Ig-secreting human hybridomas were obtained and it was possible to distinguish clones producing antibody reactive with intracellular antigens versus those reactive with cell surface antigens. In a study in which over 4,350 such clones were produced, the majority of the monoclonal antibodies were reactive with intracellular antigens which exhibited broad distribution. A limited number were reactive with cell surface antigens exhibiting a restricted distribution (Cote, et al., 1986). In some cases, "probable" specific cell surface antigens of ovarian cells have been identified with which a monoclonal antibody reacts (Smith, 1987). Another approach attempted to improve the ratios of monoclonal antibodies directed at tumor cell surface antigens by injection of autologous tumor cells admixed with *Bacillus Calmette-Guerin* (Hanna, et al., 1985).

Most recently, investigations have focused on not only the identification of antigens recognized by human monoclonal antibodies derived from gynecological tumors but also on the cellular localization of these specific antigens. In one particular case, the monoclonal antibody had been previously shown to react with a variety of tumors and established cell lines and therefore lacked tumor specificity. However, the specific antigens were distributed on regions close to the cell surface membrane and some antigens may have been exposed on the cell's surface (Aotsuka and Hagiwara, 1988).

b. Viral Oncolysates

In a distinct line of investigation, an approach to antitumor therapy based upon a biological response modification using viral augmentation has been investigated. As first demonstrated in animals, immunogenicity of tumor cell extracts is enhanced by infecting the tumor cells with selected viruses such as influenza virus, vesicular stomititis virus, Newcastle disease virus and vaccinia.

Humans receiving allogeneic extracts of cultured tumor cells similar to their own tumors also showed intensified delayed-type hypersensitivity reactions. Studies have shown that delayed-type hypersensitivity reactions are augmented in ovarian cancer patients injected with viral oncolysate derived from influenza virus-modified ovarian carcinoma cultures Freedman, et al., 1984). Furthermore, possible therapeutic applications have been investigated in various tumors, including the treatment of malignant melanoma using Newcastle disease virus oncolysate and in the treatment of vulvar carcinoma, squamous carcinoma and others.

Various novel oncolysate preparations have been described in disclosures relative to its use in the treatment of cancer. For example, Wallack (1983) described a viral oncolysate vaccine for stimulating the immune mechanism of mammals to species-specific tumors. The vaccine was prepared by infecting monolayers of tumor cells with live vaccinia virus (a non-surface budding virus), incubating for three to five days and collecting the lysate in the form of a supernatant obtained after centrifugation of the lysed cellular debris. The vaccine prepared in this manner was employed to treat species-specific tumors, apparently through stimulating the immune mechanism of the tumor burdened animal (Freedman, et al., 1988a).

In a co-pending patent application in which a co-inventor of the present invention was also a co-inventor (U.S. Pat. application Ser. No. 07/336,045, now abandoned), a novel aspect of the viral augmentation was disclosed. This is achieved by modifying the surface membranes of selected allogeneic, cultured ovarian tumor cells through the use of the influenza virus which permits cellular disruption at the time of peak cell surface membrane antigen modification. The viral-infected ovarian tumor cells are extracted and the lysate is administered to an individual having an ascites-bearing ovarian tumor in order to elicit the appearance of a soluble antitumor factor into the ascites fluid. It has been possible, as well, to demonstrate tumor surface reacting antibodies in the serum of patients following vaccination with influenza viral oncolysate (Ioannides, et al., 1989).

As described above, most of the human monoclonal antibodies which have been described in the literature have been generated against cytosolic or internal type antigens. Antibodies directed against surface binding molecules have been isolated and characterized relatively infrequently, although these appear to exhibit more specificity. None of the approaches described in the prior art to date have achieved a method capable of efficient, rapid production of these "tailor-made" reagents for use in gynecological treatment.

In order to achieve such reagents, procedures are needed which rapidly generate not only reagents which are species-specific and tumor-specific but also which are specific for cell-surface, malignant-differentiation epitopes. No procedure in the prior art teaches or suggests how to routinely achieve such diagnostic and therapeutic monoclonal antibodies designed specifically for individual patients via a process capable of rapidly generating the required "tailor-made" immunological reagents.

The present invention provides a process for the preparation and use of novel tumor diagnostic and anti-tumor reagents. The invention generally relates to the establishment of stable B cell hybridomas capable of producing human monoclonal antibodies reactive with cell surface epitopes of human gynecological tumors. A human monoclonal antibody as used herein is an antibody generated through the fusion of human lymphocytes with drug-resistant cell lines of human, mouse or human-mouse (heteromyeloma) myeloma cells. A cell surface epitope as used herein is an antigenic determinant which is found on the surface of a non-disrupted or non-permeabilized cell. More particularly, the invention provides a rapid process for generating monoclonal antibodies derived from patient-specific tumors.

In certain aspects, the invention relates to a process for obtaining human monoclonal antibodies. The process of the invention is designed to produce monoclonal antibodies whose specificity is directed against cell surface epitopes of intact gynecological tumor cells. Furthermore, it is an objective of the present invention to produce monoclonal antibodies which exhibit a cytotoxic specificity for gynecological tumors and which may be used in a treatment protocol. More specifically the invention provides a process for generating such antibodies which are tailored to the tumor of the individual patient or patient's with similar tumors, and are thus patient-specific or relatively tumor group-specific. It is another objective of the present invention to produce immunodiagnostic reagents specific to the antigens of gynecological tumor cells.

In a preferred embodiment, the process of the invention provides for the preparation of a viral oncolysate as a first step in the preparation of group-specific hybridomas. Although the use of the viral oncolysate as a first step is preferred, practice of the invention includes obtaining a hybridoma capable of producing a monoclonal antibody which is specific for cell surface antigens without use of the viral oncolysate pretreatment.

In order to produce the viral oncolysate, a gynecological tumor cell line is infected with a virus capable of inducing cell surface budding and of inducing antigenicity in the recipient. Cell surface budding is a phenomenon which may be induced in virally-infected cells where the life cycle of the virus is initially non-lysogenic. The virus must be capable, as well, of inducing antigenicity in the patient by virtue of antigens present on the viral particles or otherwise as a result of the viral infection process. The gynecological tumor cell line may be any one of a number of such cell lines known to those of skill in the art. However, in a preferred embodiment, the physician chooses a tumor cell line derived from a tumor similar to that of the patient who is to be treated. These cell lines may be one of any of the established immortalized cell lines derived from gynecological tumors such as SW756, CaOV$_3$ and MDAH 2774. Most preferably, the cervical carcinoma cell line SW756 is infected where an antibody is desired which will have specificity for cervical tumors. Likewise, where an antibody is desired which will have specificity for ovarian tumors, CaOV$_3$, SKOV3 or MDAH 2774 are most preferably used.

Although, numerous viruses may meet the qualifications of the invention, the invention is preferably practiced using a strain of influenza virus A, such as a Puerto Rican strain, or the Newcastle Disease virus. After infection of the chosen tumor cell line with the chosen virus, a lysate of the infected cells is produced giving rise to the viral oncolysate of the invention.

A second step of the process for obtaining the monoclonal antibodies of the invention allows for injecting a patient having a gynecological tumor with the viral oncolysate. This treatment involves injecting a given amount of viral oncolysate into the patient via an injection regime designed to elicit an immune response from the patient. The injection regime can take any of a number of different routes known to those of skill in the art. However, in a preferred embodiment, the injection of viral oncolysate into the patient will be by intralymphatic administration directly into the lymph system of the patient when the patient possesses a cervical tumor. Likewise, when the patient possesses an ovarian tumor, administration of the viral oncolysate will be by intraperitoneal administration.

After sufficient time has elapsed for the patient treated with viral oncolysate to have produced the desired immune response (usually 5–10 days post-treatment), a source of lymphocytes is removed from the patient. The tissue obtained from the patient as a source of lymphocytes may include any of a number of such sources but preferably will be peripheral blood, lymph nodes or bone marrow. Because of its rapidity and ease of extraction and because of the minimal intrusion required into the patient's body, peripheral blood is a more preferred source of the lymphocytes of the invention.

An important aspect of the invention is the discovery of a means for enhancing the hybridoma frequency from peripheral blood lymphocytes capable of secreting surface-specific antibodies. Lymphocytes of the peripheral blood appear to be an unsatisfactory fusion source when stimulated in vitro with any number of mitogens including B cell mitogen and pokeweed mitogen or with treatment of the blood lymphocytes with irradiation. In a preferred embodiment, patients will receive intralymphatic vaccination with viral oncolysate and produce a hybridoma growth rate of 28–44% of the total number of wells plated when peripheral blood lymphocytes are utilized for the fusion. Alternatively, patients may receive viral oncolysates augmented with interleukin II (Cetus Corp., Emeryville, Calif. 94608) for enhancement of immune response via B cell mediated-effects.

After removing the source of lymphocytes from the patient undergoing treatment, the cultured lymphocytes of the patient are fused with an appropriate fusion partner to provide the requisite hybridomas. The fusion process may involve a number of alternative procedures known to those of skill in the art but will generally involve polyethylene glycol-mediated fusion of a lymphocyte and a myeloma-derived cell. Subsequently, fused cells are selected by drug-resistance until a collection of hybridoma colonies is produced. In a preferred embodiment, the fusion partner cell line will be derived from human cells. In its most preferred embodiment, the human fusion partner will be the heteromyeloma cell line SPAZ 4 of the Sandoz Institute (Sandoz Research Institute, East Hanover, N.J.).

Once hybridomas have been produced via fusion of the patient's lymphocytes with an appropriate fusion partner, the resulting clones are screened for the presence of monoclonal antibodies directed against gynecological tumor cells. The screening is accomplished by testing the antibodies secreted by the hybridoma clones against well-characterized immortal gynecological tumor cell lines. The cell lines used to screen for tumor cell-surface reactivity may be any of a number of such cell lines known to those of skill in the art including the cell lines SW756, MDAH 2774, CaOV$_3$ (ATCC Accession No. HTB 75) SKOV3 (ATCC Accession No. HTB77) CaOV$_3$ (ATCC Accession No. HTB 77) and SKUT-1 (ATCC Accession No. HTB 114).

Furthermore, while pre-treatment of a patient with a viral oncolysate is a preferred step prior to screening for cell surface antigens, it should be noted that the process can be practiced successfully on hybridomas which are derived from patients who have not been so pre-treated. In one embodiment of the invention, it is possible to screen any hybridoma derived from a gynecological cancer patient for cell surface antigens selective for a particular cancer cell line.

It is to be noted that the process as described above will generate reagents which possess certain characteristics and which will be useful in a number of research and clinical situations. For instance, the monoclonal antibody derived by the process of the present invention is capable, in most instances, of specifically binding the cell surface epitopes of intact tumor cells. As such, the monoclonal antibody of the invention is capable of being used as a reagent in a diagnostic technique for detection of gynecological tumors.

A further embodiment of the invention, therefore, is a method of diagnosing the presence of a gynecological tumor. The monoclonal antibodies of the invention may be complexed with the cells of a patient and, after an appropriate incubation time, subjected to a diagnostic technique capable of detecting immunocomplexes. An immunocomplex as used herein refers to the specific complex of the human monoclonal antibody reagent with the gynecological tumor cell of the patient by virtue of the specific cell surface epitopes on the surface of the patient's cells which are reactive with the antibody. The monoclonal antibody may be used to localize tumor cells on microscopic examinations where the cells have been disrupted or fixed, as well. However, diagnostic techniques relying on the presence of intact, non-fixed cells such as in vivo labelling, microscopic fluorescence, enzyme linked immunoassay and cell sorting will be particularly enhanced by use of the cell surface specific monoclonal antibodies of the invention.

The present invention can also be used to provide monoclonal antibodies useful in immunotoxin treatments where the antibodies act as vehicles for toxins or drugs. An alternative approach for therapy is the use of anti-idiotype antibodies which may be used to activate an idiotype response resulting in tumor cell death. In a preferred embodiment, however, cytotoxicity of the antibody of the invention is achieved in conjunction with complement-dependent cytotoxicity.

The process of the invention further provides for the production of hybridoma cell lines capable of secreting the monoclonal antibodies of interest. The cell lines produced should be stable for up to 3 months of continuous growth and monoclonal antibody production. Antibody producing hybridomas can be maintained for more than one year with regular recloning. The cell line should also be capable of undergoing freezing and thawing in order to maintain the cell line for extended periods of time. This is an important aspect of the invention, since therapy of gynecological tumors and the use of the antibodies as diagnostic reagents may take place over extended time periods. Also, having once generated a patient-specific reagent such as that described by the invention, the physician may desire to maintain cultures for potential follow-up therapy at much later dates. Recent advances in molecular biology provide the possibility of molecular cloning and gene sequencing of antibodies found by methods such as described here to provide unlimited supplies of the antibodies (Boulianne, et al., 1984; Morrison, et al., 1984; Neuberger, et al., 1984).

The monoclonal antibodies of the present invention may also be produced using recombinant DNA technology. Where large-scale production of such antibodies is required, it is believed that certain advantages will be obtained by expression of DNA segments encoding the monoclonal antibodies in recombinant expression systems. Typically, the heavy (VDJ) and light (VJ) cDNAs are amplified (e.g., using polymerase chain reaction), followed by cloning of the amplified DNA and subsequent sequencing. Once the segments are cloned and sequenced, appropriate expression systems are selected and the genes are subcloned into them for use in large-scale production.

The invention further provides for a method of treating a patient having a gynecological tumor. As described above, the physician using the therapy of the invention will first inject the patient with the viral oncolysate of a gynecological tumor cell line. After an appropriate time is allowed for immune response, a lymphocyte source is removed from the patient, lymphocytes are cultured from this source and subsequently fused with an appropriate fusion partner in order to produce a collection of hybridomas capable of secreting the desired monoclonal antibodies. The monoclonal antibodies of these hybridomas are then screened for their ability to bind to surface epitopes of known gynecological tumor cell lines. The physician may then treat a patient possessing a similar tumor with the monoclonal antibody of choice.

It is, of course, recognized that monoclonal antibodies so derived may be used in diagnoses and therapies where the patient's own body is the source of the fusing lymphocytes where extended or recurring illness occurs. Alternatively, the monoclonal antibodies of the invention may be used to treat a patient different from the patient whose body provided the source of lymphocytes. This is particularly true where the monoclonal antibody reagent is being used as an immunodiagnostic tool.

Finally, it is also possible to utilize the processes of the invention to determine the degree of similarity of epitopic specificity between a monoclonal antibody of unknown specificity and a reference monoclonal antibody of a defined specificity which has the desired characteristics of cell surface binding of gynecological tumor cells. Using this approach, the advantages of the present invention in obtaining rapidly cell surface binding monoclonal antibodies specific to tumor and patient may be amplified.

The processes of the invention, therefore, are dependent upon the specificity of a human monoclonal antibody for gynecological tumor cells. The requisite specificity results from an affinity of such monoclonal antibodies for a cell surface epitope on the surface of gynecological tumor cells. In particular aspects, the cell surface epitope will be the result of the presence of cell surface polypeptides identical or substantially similar to cell surface polypeptides found on the surface of SKOV3 cells which polypeptides migrate as an approximately 32 Kd band when electrophoresed through a gel. At least one such epitope is described herein which has been found to be associated with a cell-surface glycoprotein. The affinity of such monoclonal antibodies for the cell surface epitopes may be characterized by an association constant. In studies using the AC6C3 monoclonal antibody of the present invention, such an association constant has been found to have a value range of approximately $2.0\text{--}3.0 \times 10^{10} \text{ M}^{-1}$.

BRIEF DESCRIPTION OF DRAWINGS

The file of this patent contains at least one drawing executed in color. Copies of this patent with color drawings will be provided by the Patent and Trademark Office upon request and payment of the necessary fee.

FIG. 6A. Immunoprecipitation. A. Lanes in A are; a=human MAb negative control (H1), b=human anti-ovarian MAb (AC6C3).

FIG. 6B. Western Blotting. B. Lanes in B are; a=negative control (no human IgM), b=human MAb control (H1) and c=human antiovarian MAb (AC6C3).

VIRAL ONCOLYSATE

Preparation

Figure 1A:
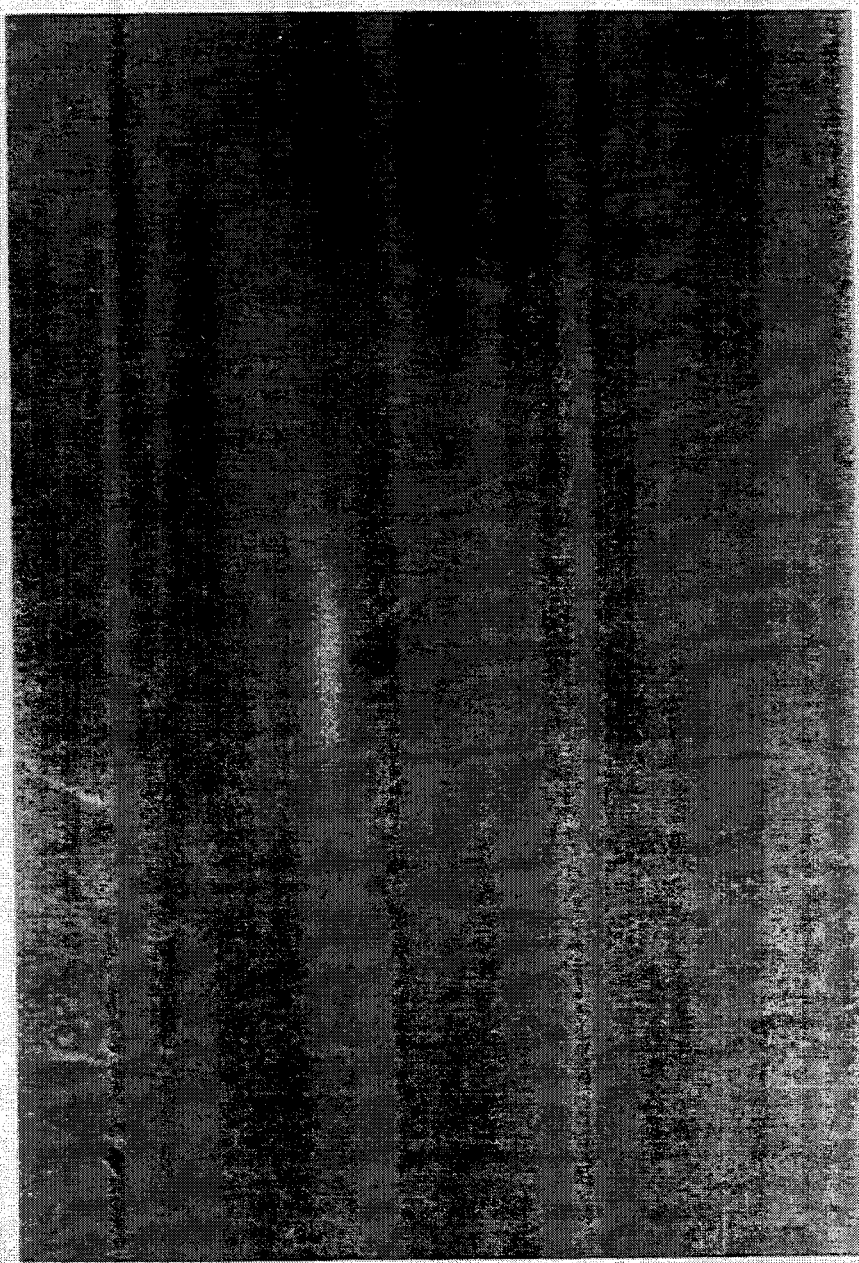
FIG. 1A. Immunofluorescence Assay. Brightfield microscopy of SW756 cells treated with CR (4E8E10) hybridoma supernatant.

The preparation of viral oncolysate (VO) is well-known in the art and may be prepared according to a previously described procedure (ovarian—Freedman, et al., 1988a; cervical—Freedman, et al., 1989). The characterized uterine cervical carcinoma cell line SW756, which supports infection with the Puerto Rican strain PR8 of influenza A virus, is typically used as the immunogen (SW756—Freedman, et al., 1982; intralymphatic injection—Freedman, et al., 1988b).

In a procedure which the applicants have found to work well, cells are infected in the exponential phase after 48 hours incubation in serum-free medium. Cells are infected with 5 ml per flask of a dilution from the frozen-stock virus in phosphate-buffered saline sufficient to give approximately $1 \times 10^5$ $EID_{50}$ (per 50% egg-infective dose) per flask. Infected cultures are incubated at 35° C. for 20 hours and then scraped off the flask. Cell suspensions are centrifuged at 300 xg and supernatants are discarded. The pellets are resuspended in an equal volume of 0.001 M $MgCl_2$.

A volume of DNase (Worthington, Freehold, N.J.) at 1 mg/ml equal to the pellet volume is then added, followed by a volume of 1.8N NaCl equal to the cell pellet DNAse suspension volume. The resulting suspension is sonicated at 310 kHz for 3 minutes on ice. Sonicates are irradiated in a petri dish under an ultraviolet lamp set to deliver $4 \times 10^{-6}$ $Jsec^{-1}m^{-2}$ and a fluid depth of less than 3 mm. Lysates are pooled and dispersed into vials at a concentration of 1.5 mg protein in 1 ml of the NaCl solution) and stored at −70° C. until needed. All batches are checked for bacteria by subculture according to the procedure described in *Federal Register*, Vol. 38:P 32056, para. 610, 12.

Schedule and Route of Administration

VO is administered at a dose of approximately 1.5 mg by intradermal injection alternately to the anterior thighs. Injections are given on alternative weeks until completion of irradiation, then monthly up to 12 months following the initiation of irradiation therapy. Vaccine is administered to patients by a research nurse during any week that includes a hospital visit, and self-administered, following instruction by the research nurse, during other weeks. Alternatively, an intralymphatic route may be used with doses of approximately 1.5 to 6.0 mg or an intraperitoneal route may be used with doses of approximately 9.0 mg.

OTHER LYMPHOCYTE SOURCES

Bone Marrow

Bone marrow buffy coats are frozen in liquid nitrogen in vials containing $40 \times 10^6$ cells. When ready for use, frozen vials are air-dried for 2-3 minutes then thawed quickly in a 37° C. water bath while shaking. The contents of one vial are aseptically transferred to a first tube (No. 1) containing 8.0 ml of Hank's Balanced Salt Solution (HBSS; Gibco, Grand Island, N.Y.) 20% FBS (Fetal Bovine Serum, Hyclone, Provo, Utah), 10 U/ml of heparin and 20 U/ml DNAse (DNAse I, Type II Sigma 4527, Sigma Chemical Co., St. Louis, Mo.). DNAse is typically made up in a 0.02% solution (0.2 mg/ml, 500 U/ml). Heparin (Invenex Laboratories, Melrose Park, Ill.) is supplied as 1000 U/ml solution. The resulting cell suspension is placed in a 37° C. incubator for 1.5 hours.

After incubation, the contents of tube no. 1 are layered onto a 15 ml second tube (No. 2) containing 3.0 ml of Ficoll Hypaque (FH 1077; Sigma Histopaque 1077, Sigma Chemical Co., St. Louis, Mo.) and are centrifuged at 700 xg for 15 minutes at room temperature.

The resulting interface is placed in a 15 ml third tube (No. 3) containing 8.0 ml of HBSS plus 1% FBS and centrifuged at 200 xg for 10 minutes at room temperature. The resulting cell pellet is ready for use in the Epstein-Barr virus transformation procedure (infra).

USE OF THE SPAZ 4 FUSION PARTNER

Maintenance

SPAZ 4 is a heterohybridoma (mouse myeloma × human peripheral blood lymphocytes) obtainable from Sandoz Institute. For maintenance, the SPAZ 4 cells are grown in Iscove's Modified Dulbecco's Medium (IMDM; Gibco, Grand Island, N.Y.) containing 5% FBS and are passed twice a week at a 1:40 split in a T75 flask (Becton Dickinson, Lincoln Park, N.J.). When passing, the cells should be vigorously pipetted in the flask to loosen any attached cells.

Three weeks prior to the use of the cells for fusion, 20 ug/ml of 8-azaguanine (Sigma Chemical Co., St. Louis, Mo.) are added to the culture medium. The 8-azaguanine stock is typically made up as a 2.0 mg/ml solution of which 5 ml of the stock are used per 500 ml medium. Three days prior to the use of the cells for fusion, the medium should be changed to IMDM+10% FBS.

Hybridoma Medium

A 500 ml stock of the hybridoma medium for use with SPAZ 4 fusions can be made up by combining 344 ml of IMDM, 100 ml of FBS (to a final concentration of 20%), 0.5 ml of a 5 mg/ml insulin stock (to a final concentration of 5 ug/ml), 50 ml of NCTC 109 medium (to a final concentration of 10%; Sigma Chemical Co., St. Louis, Mo.), 0.5 ml of a 5 mg/ml transferrin stock (5 ug/ml final concentration), 5.0 ml of a hypoxanthine stock (infra), 0.5 ml of an aminopterin stock (infra), and 1.0 ml of a thymidineglycine stock (infra).

HAT Ingredients

The stocks of HAT ingredients may be prepared as follows. A 0.136 g amount of hypoxanthine is placed in 100 ml of deionized water and the mixture is heated in a boiling water bath or over a flame until dissolved. After cooling the solution to room temperature, it is filtered through a 0.22 um filter, divided into 5 ml aliquots and stored at −20° C.

Aminopterin, which is supplied as methotrexate in a 25 mg/ml solution (Quad Pharmaceuticals, Indianapolis, Ind.) is used at a ratio of 0.1 ml/100 ml medium. The resulting 1 X solution of aminopterin in the medium kills the unfused SPAZ 4 cells.

Thymidine-glycine stocks are prepared by adding 0.387 g thymidine and 0.0255 g glycine to near-boiling, deionized water until both ingredients are dissolved. The cooled solution is then filtered through a 0.22 um filter, divided into 1.0 ml aliquots and stored frozen in 1 ml aliquots at −20° C.

Wash Solution

The wash solution used herein is made up by adding 35 ml of a 0.1% Versene stock solution to 400 ml of RPMI 1640 Medium w/L-glutamine (Gibco, Grand Island, N.Y.). A 1% Versene stock solution is made up by dissolving 1 g EDTA in 100 ml of water. The 0.1% Versene stock is made up by adding 10 ml of 1% Versene to 90 ml of RPMI.

Hybridoma Cloning Procedures

Method 1 (Mini-cloning):

In order to clone hybridomas, the thymus is surgically removed from one BALB/C mouse and minced with a 25 gauge hypodermic needle in 10 ml RPMI containing 10% FBS. After centrifugation at 460 xg for 5 minutes at room temperature, the supernatant is aspirated off and the cell pellet is resuspended in 0.5 ml RPMI containing 10% FBS in a 5 ml snap cap tube (Becton Dickinson, Lincoln Park, N.J.). The tube containing the cells is then irradiated with 10,000 rads.

The irradiated thymus cells are then resuspended in 14 ml of hybridoma medium without HAT and 0.1 ml of the suspension (approximately 2 drops from a 10 ml pipet) is added to each well of one 96-well tissue culture plate (Becton Dickinson, Lincoln Park, N.J.). This should yield about $3.5 \times 10^5$ thymocytes per well.

A volume of 0.2 ml of suspended hybridoma cells from one mother hybridoma well is removed. This volume is brought up to 6.0 ml with hybridoma medium without HAT giving a 1/30 dilution. Three 1/10 serial dilutions of the 1/30 stock are made using hybridoma medium without HAT to give dilutions of 1/300, 1/3000, and 1/30,000. These serial dilutions are most easily accomplished by adding 1 ml of the 1/30 stock to 9 ml of hybridoma medium without HAT giving a 1/300 dilution, etc.

To each well in the first three columns of the 96-well plate containing the thymus cells, 0.1 ml (2 drops from a 10 ml pipet) of the 1/30 dilution is added. Similarly, 0.1 ml of the 1/300, 1/3000 and 1/30,000 dilutions is added to the wells in the second, third and fourth set of three columns of wells each, respectively.

The plates so constructed are incubated at 37° C. in $CO_2$ for 7 days and then checked for growth microscopically. The number of colonies per well is recorded. When growth is sufficient to turn media yellow, the supernatants from the positive wells are checked by ELISA (infra) for antibody production. Wells which are scored positive by ELISA are then checked by IF (infra) for surface-binding antibodies.

Method 2 (One Cell Per Well Cloning):

In order to clone hybridomas via a one cell per well cloning method, the thymus is surgically removed from one BALB/C mouse and minced with a 25 gauge hypodermic needle in 10 ml RPMI containing 10% FBS. After centrifugation at 460 xg for 5 minutes at room temperature, the supernatant is aspirated off and the cell pellet is resuspended in 0.5 ml RPMI containing 10% FBS in a 5 ml snap cap tube. The tube containing the cells is then irradiated with 10,000 rads.

The irradiated thymus cells are then resuspended in 14 ml of hybridoma medium without HAT and 0.1 ml of the suspension (approximately 2 drops from a 10 ml pipet) is added to each well of one 96-well tissue culture plate. This should yield about $3.5 \times 10^5$ thymocytes per well.

The contents of one hybridoma mother well are removed and the number of cells is counted using a hemacytometer slide. The cell concentration is adjusted to 10 cells/ml with hybridoma medium without HAT and 0.1 ml of the resulting suspension is added to each well.

The plates so constructed are incubated at 37° C. in $CO_2$ for 7 days and then checked for growth microscopically. The number of colonies per well is recorded. When growth is sufficient to turn media yellow, the supernatants from the positive well are checked by ELISA (infra) for antibody production. Wells which are scored positive by ELISA are then checked by IF (infra) for surface-binding antibodies.

FUSION PROCEDURES

Lymph Node X SPAZ 4
Part A:

A lymph node from a patient suspected of having a gynecological tumor is minced in RPMI 1640 medium containing 10% FBS. The suspension is then centrifuged for 5 minutes at 2,000 rpm (820 xg) at room temperature and washed twice with wash solution, centrifuging each time at 1,500 rpm (460 xg) at room temperature for 5 minutes. The cells are then resuspended in wash solution and counted using a Coulter Counter (Coulter Electronics, Hialeah, Fla.).

Part B:

The SPAZ 4 cells are detached from the walls of the plastic flask by vigorously tapping the flask in which they are growing. The resulting suspension is centrifuged at 1,500 rpm (200 xg) for 5 minutes at room temperature. The cell pellet is washed twice with wash solution, centrifuging each time at 1,000 rpm (200 xg) for 5 minutes at room temperature. The cell pellet is resuspended in 10 ml of wash solution and counted using a hemacytometer slide.

Part C:

The lymphocytes and SPAZ 4 cells are combined at a 1:1 ratio, saving some of each to plate as controls. The combined cell suspension is centrifuged at 1,000 rpm (200 xg) for 5 minutes at room temperature and 1 ml of polyethylene glycol (PEG 1500, Boehringer Mannheim, (Indianapolis, Ind.) is added dropwise for one minute maintaining the tube containing the cells at 37° C. in a water bath.

A volume of 1 ml of wash solution is added to the cell suspension dropwise for 2 minutes at 34°–37° C. This is followed by the addition of 10 ml of wash solution dropwise for 5 minutes at 34°–37° C. The resulting suspension is then centrifuged at 1,000 rpm (200 xg) for 5 minutes at room temperature and the supernatant is removed.

The cells are then gently resuspended in hybridoma medium containing hypoxanthine and thymidine at a concentration of $1 \times 10^6$ cells/ml. At the same time, the control lymphocytes and SPAZ 4 cells are resuspended in the same medium at a concentration of $1 \times 10^6$ cells/ml.

Finally, 0.1 ml (2 drops from 10 ml pipet) of each cell suspension is added to wells in 96-well microtiter plates being sure to leave all outside wells empty. In the last plate it is necessary to insure that several wells of the control lymphocytes and several wells of the control SPAZ 4 are plated. The plates so constructed are incubated at 37° C. in $CO_2$.

Part D:

After two days of growth, 0.1 ml of hybridoma medium containing 2 X HAT is added to each well. Thereafter, the cells are fed twice a week (Monday and Friday is a suggested schedule) for two weeks with hybridoma medium containing 1 X HAT. At feeding times, approximately 0.1–0.15 ml of medium is aspirated from each well and replaced with new medium.

On the 7th day after fusion, the plates are checked for fusion frequency. Fusion frequency is the number of clones per $1 \times 10^6$ lymphocytes plated. After 14 days, the wells are fed twice a week (Monday and Friday) with hybridoma medium without the HAT selective ingredients added.

Part E:

ELISA screening (infra) for antibody production in wells with growing hybridomas is carried out. Immunofluorescence (IF) screening (infra) for surface binding antibodies from wells positive by ELISA screening (infra) is carried out as well.

Peripheral Blood Lymphocytes X SPAZ 4
Part A:

A volume of 30 ml of heparinized blood is centrifuged for 10 minutes at 1,500 rpm (460 xg) at room temperature. The plasma is aspirated off and discarded and the volume is brought up to 60 ml with RPMI 1640 medium. The blood mixture is layered onto tubes containing 3 ml FH 1077 by using 10 ml blood mixture per tube. The tubes containing the blood mixture are centrifuged for 20 minutes at 2,000 rpm (820 xg) or for 40 minutes at 1,500 rpm (200 xg) at room temperature using slow acceleration. The lymphocyte interface is removed and washed twice with phosphate buffered saline (PBS; Gibco, Grand Island, N.Y.) without calcium or magnesium, centrifuging each time at 1,500 rpm for 5 minutes at room temperature. The cells are resuspended in 10 ml of wash solution and counted using a Coulter Counter. Parts B, C, D, and E described supra for the lymph node fusion procedure are then followed.

Epstein-Barr Virus Transformation Procedure

Separation of B cells from whole blood:

A volume of 180 ml blood is obtained from a donor (e.g., an ovarian cancer patient in remission). The Ficoll Hypaque separation procedure for peripheral blood lymphocytes (supra) is followed to obtain lymphocytes. The adherence procedure for removal of macrophages (infra) is then carried out. The AET rosetting procedure (infra) is followed to separate B cells from T cells. The resulting B cells may be stored overnight at a concentration of $20 \times 10^6$ cells in 20 ml RPMI containing 10% FBS at 4° C. Prior to use, the cell suspension is centrifuged for 5 minutes at 1,000 rpm (200 xg) at room temperature and the supernatant is discarded.

Separation of B cells from frozen bone marrow:

The procedure for obtaining B cells from bone marrow buffy coats (supra) may be used instead of the whole blood in the procedure above. Thereafter, the procedure is identical to that above.

EBV Transformation procedure:

EBV B 95-8 may be obtained from Showa University Research Institute (St. Petersburg, Fla.). One vial contains $1 \times 10^8$ Transforming Units (TFU) in 0.2 ml. The contents of a vial of virus are diluted to 20 ml (1:100 dilution) with RPMI containing 10% FBS and $20 \times 10^6$ B cells are then added to the EBV solution in order to obtain 5 TFU/B cell. The resulting cell suspension is then incubated in 37° C. waterbath for 2 hours. The cells are washed once with PBS and centrifuged at 1,500 rpm (460 xg) for 5 minutes at room temperature. The cell pellet is resuspended in RPMI containing 10% FBS at a concentration of $2.5 \times 10^5$ cells/ml in 80 ml.

One T75 flask of confluent MRC-5 fetal lung fibroblast cells (ATCC Accession No. CCL171) are used as feeder cells and are removed from the flask by trypsinizing. The resulting cell suspension is centrifuged at 1,500 rpm (460 xg) for 5 minutes at room temperature and the cell pellet is resuspended in 0.5 ml RPMI containing 10% FBS in a 5 ml snap cap tube. The MRC-5 cells are irradiated with 4500 rads and $3.2 \times 10^6$ of the irradiated MRC-5 cells are added to the transformed B cell suspension. This should yield $4 \times 10^4$ MRC-5 cells/ml.

A volume of 0.2 ml (2 drops from a 10 ml pipet) of the resulting cell suspension is added to all wells in 96-well plates giving the following approximate concentrations of cells per well:

Number of EBV Transformed B cells/well = $5 \times 10^4$
Number of Irradiated MRC-5 cells/well = $8 \times 10^3$ The cells are fed twice a week with RPMI containing 10% FBS by first aspirating off 0.1 ml of old medium then adding back 0.1 ml new medium. Growth should begin to appear from 1-3 weeks after transformation. All growing wells are checked using ELISA (infra) and all positive wells are expanded to a 24-well plate. Positive ELISA wells are then checked using the immunofluoresence assay (infra) and all wells positive by immunofluoresence are expanded to a T75 flask using RPMI containing 10% FBS. Fusion with the SPAZ 4 fusion partner may then be attempted (supra).

DIAGNOSTIC TECHNIQUES

Immunoglobulin ELISA Procedure

Suppliers for materials found in the procedures below are as follows:
Cappel (Malvern, Pa.)
Tago (Burlingame, Calif.)
Kirkegaard & Perry (Gaithersburg, Md.)
Gibco (Grand Island, N.Y.)

Procedure:

The wells of a 96 well plate are coated with 100 ul of 10 ug/ml goat anti-human total immunoglobulins (Cappel) or specific goat anti-human Ig's (Tago) in order to quantitate or subtype. The upper left well should be left blank.

The plate is next refrigerated at 4° C. overnight then each well is blocked with 300 ul of PSG (Gibco) containing 10% FBS for 2 hours at room temperature. Blank wells are left empty. A Titertek Multichannel Pipet (Flow Laboratories, McClean, Va.) may be used to fill wells while blocking. Using a Cornwall Syringe, the plate is washed twice with 250 ul of PBS containing 0.02% Tween 20 (Kirkegaard & Perry) per well followed by a wash with 250 ul of PBS per well.

A volume of 100 ul of test supernatants, dilutions of control serum, or dilutions of purified IgA, IgG, or IgM (Cappel) is added if one wishes to make a curve from the O.D. values for quantitation purposes. A volume of 100 ul of PSG containing 10% FBS is added to negative control wells. Blank control wells are left empty. The plate is incubated for 2 hours at room temperature then washed twice with 250 ul of PBS containing 0.02% Tween 20 followed by washing twice with 250 ul of PBS.

A volume of 75 ul of peroxidase-labeled total immunoglobulins (Kirkegaard & Perry) or specific peroxidase-labeled immunoglobulin (Tago) is added if one is going to quantitate or subtype at a 1:3000 dilution with PSG containing 10% FBS for 2 hours at room temperature. Blank wells are left empty. Wells are then washed 3 times with 250 ul of PBS containing 0.02% Tween 20 followed by washing 3 times with 250 ul of PBS alone.

Approximately 100 ul of ABTS substrate (Kirkegaard & Perry) is then added and allowed to remain in all wells for 30 minutes at room temperature in the dark. The plates should be gently swirled to evenly distribute the dye. The results are then read on an ELISA reader at O.D. 405 and 490 nm.

Indirect Immunofluorescence Procedure

A concentration of $1-2 \times 10^4$ cells/well are plated in a 48-well microtiter plate (Costar, Cambridge, Mass.) 2 days before testing. Four drops (0.2 ml) of medium from a 10 ml pipet are added to each well followed by addition of the same amount of cell suspension (0.2 ml at a concentration of $5 \times 10^4$ or $1 \times 10^5$ cells/ml) to each well. The plate is then wrapped in foil and incubated at 37° C. for 2 days. Cells should be about 50% confluent when ready.

Using an Eppendorf Pipeter (Brinkmann Instruments, Westburg, N.Y.), each well is washed 3 times (0.25 ml each time) with cold PBS containing 0.02% $NaN_3$. Washes are accomplished with a micropipet tip attached to a vacuum flask. A micropipet tip is used to aspirate off the last PBS wash from one row at a time in the plate. Immediately, then, a volume of 110 ul of sample supernatants, control serum (1:10 dilution), or PBS containing 0.02% NaN$_3$ (for negative controls) is added to the wells. The plate is then refrigerated at 4° C. for 60 minutes.

The supernatants from each well are then aspirated off and the plate is washed 5 times (0.25 ml/well each time) with cold PBS containing 0.02% NaN$_3$. A volume of 110 ul fluorescein-conjugated antibody (Tago Goat Anti-Human Total Ig, FITC Conjugated) is added to each well at a 1:40 dilution with PBS containing 0.02% NaN$_3$. The plate is then refrigerated at 4° C. for 60 minutes. The FITC antibody is then aspirated off and the plate is washed 3 times (0.25 ml/well each time) with cold PBS containing 0.02% NaN$_3$.

The plate is fixed with 110 ul/well of a 3.5% formaldehyde solution at room temperature for 30 minutes. A 3.5% formaldehyde (20% Ultrapure TEM Grade, Tousimis Research Corp., Rockville, Md.) solution can be made up by adding 10 ml of 20% formaldehyde to 47 ml of PBS containing 0.02% NaN$_3$. The plate should be kept covered with foil. When ready for viewing, the plate is washed three times with room temperature PBS containing 0.02% NaN$_3$. Prior to microscopic examination, the wells are covered with 90% glycerol in NaHCO$_3$, pH 8.0 (0.3 ml/well).

Results are read on an Olympus IMT-2 inverted microscope with reflected light fluorescence attachment, blue excitation filters BP490 and EY455, barrier filter O-515 and autoflourescence cut filters (Olympus, Lake Success, N.Y.) at a magnification of 100 X.

Indirect Immunoperoxidase Procedure

Preparation of Slides (Paraffin Sections):

Paraffin-embedded tissues are cut and mounted on slides. The slides are heated at 54°-58° C. for 30-60 minutes then dipped in 3 changes of xylene for 10 minutes each. The slides are then dipped in 2 changes of 100% ethyl alcohol (EtOH) for 10 minutes each followed by dipping in 2 changes of 95% EtOH for 5 minutes each. The slides are then dipped in 1 change of 90% EtOH for 5 minutes followed by dipping in 1 change of 75% EtOH for 5 minutes.

Preparation of Slides (Cell Lines):

Cells to be examined are scraped from the culture flask. Importantly, the cells should not be trypsinized. The resulting cell suspension is then centrifuged for 5 minutes at 1500 rpm (460 xg) and the cell pellet is resuspended in RPMI serum-free medium. The cell concentration is determined by making a hemacytometer count and the concentration of cells is adjusted to $1.25 \times 10^5$ cells/ml. A volume of 0.2 ml ($2.5 \times 10^4$ cells) is added to each bucket containing a microscope slide and the bucket is placed in a cytocentrifuge (Shandon Cytospin, Shandon Co., Pittsburgh, Pa.) and centrifuged at 750 rpm for one minute. This attaches the cells to the slide. The slides are then air-dried and fixed in cold acetone for 10 minutes at 4° C. and dried again. The slides may be stored in this condition at −70° C. When removed from the freezer, the slides to be stained should be allowed to stand at room temperature for 5–10 minutes. To help prevent overflowing of liquids, cells on the slides should be ringed with a diamond pencil.

Preparation of Slides (Frozen Sections):

The microtome knife to be used in sectioning should be stored at −20° C. for 24 hours prior to use. Frozen embedded tissues are cut into sections approximately 6 microns thick. Tissue sections are placed on slides coated with poly L-lysine (Sigma Chemical Co., St. Louis, Mo.) or Chrome Alum-Gelatin Adhesive (EM Science, Cherry Hill, N.J. and Difco Lab., Detroit, Mich.). The slides are fixed in a 1:1 solution of methanol and ethanol for 4 minutes at room temperature. Slides may also be left unfixed. In either case, the slides are allowed to air dry for 10 minutes. After such preparation, the fixed slides may be stored flat at −20° C. or −70° C. for up to 6 months. Unstained slides should be immediately fixed.

Immunoperoxidase Staining Procedure:

After fixation, the slides are washed in PBS for 5–20 minutes in a staining dish in which a paper clip on the bottom of the dish is used to stir the washing solution when placed on a stirring plate. Blocking solution is made up using a Vector Vectastain Kit (Vector Lab., Burlingame, Calif.) by mixing 3 drops of normal goat serum with 10 ml of PBS.

The slides are placed in a plastic Nalgene box across two 1 ml pipets that are resting on moist paper towels. An amount of approximately 4–5 drops of the goat serum solution is added with a Pasteur pipet to each slide taking care to keep the solution within the diamond pencil ring. The slides so treated are then incubated at room temperature for 20 minutes.

The liquid is drained from each slide onto a paper towel and the cells are washed in PBS by swirling the slides back and forth in a staining dish. The slides are then dried off with a paper towel after which 4–5 drops of either test supernatant, positive control supernatant or negative control supernatant are added to each slide. Slides are then placed back in the covered Nalgene box with moist paper towels for 60–120 minutes at room temperature. The slides are then washed in PBS for 10 minutes at room temperature with stirring and dried off with a paper towel.

In order to prepare the Biotinylated Affinity-purified Anti-IgG or IgM from the Vector Vectastain Kit, 1 drop of Biotinylated Anti-immunoglobulin is added to 10 ml of PBS. Approximately 4–5 drops of the Biotinylated Anti-immunoglobulins are then added to each slide and incubated in the covered Nalgene box for 60–120 minutes at room temperature. Thirty minutes prior to the end of the incubation period, the Vectastain ABC reagent should be prepared by adding 2 drops of Reagent A (Avidin DH) and 2 drops Reagent B (Biotinylated Horseradish Peroxidase H) to 10 ml of PBS. The solution should be allowed to stand for 30 minutes prior to use.

Following the incubation period, the slides are washed in PBS for 10 minutes at room temperature with stirring and dried with a paper towel. Approximately 4–5 drops of Vectastain ABC reagent is then added to each slide and incubated in the covered Nalgene box for 60 minutes at room temperature.

In order to prepare the Peroxidase Substrate (Bio Genex Lab., San Ramon, Calif.), 1 drop of SA (0.5% H$_2$O$_2$) is mixed with 1 drop of SB (AEC-3-amino-9-ethylcarbazole in N,N-dimethyl formamide). This mixture is then added directly to a bottle containing 2.5 ml of SC (buffer). This reagent should be discarded after one use. The slides are then washed in PBS at room temperature for 10 minutes with stirring and dried with a paper towel. Approximately 4–5 drops of substrate are added to each slide and the slides are then incubated in the covered Nalgene box for 10 minutes at room temperature.

The slides are then washed in tap water at room temperature for 5 minutes in a staining dish with stirring and dried with paper towels. Gill's Hematoxylin No. 3

(Poly Sciences, Warrington, Pa.) is then used to counterstain the cells by adding 3-4 drops to each slide and incubating at room temperature for 3 minutes in the covered Nalgene box.

Slides are subsequently swirled in a staining dish containing tap water and dried with paper towels. One drop of Aqua Poly Mount (Poly Sciences) is added to a round cover slip and the slide (cell side down) is inverted and pressed onto the cover slip. A microscopic check is then performed for brown staining in the tissue sections. This indicates a positive reaction. For permanent storage, the cover slips should be sealed with clear finger nail polish and refrigerated in a slide box at 4° C.

Cell ELISA Procedure

The target cells are seeded at $1-2 \times 10^4$ cells/well in a 96-well plate. This is accomplished by first adding 2 drops of media from a 10 ml pipet (0.1 ml), then adding 2 drops of a $1-2 \times 10^5$ cell stock solution (0.1 ml) to each well. The upper left well should be left empty. The plate is then wrapped in foil and incubated at 37° C. for 48 hours. The medium is removed by flicking the plate in a sink.

Approximately 50 ul/well (Titertek Pipet) of a 10% solution of neutral-buffered formalin is added and allowed to remain in contact with each well for 5 minutes in order to fix the cells. Blank wells should be left empty. A 10% solution of neutral-buffered formalin is made fresh each time (each plate requires 5 ml) by mixing 1.65 ml of 37% formaldehyde with 4.5 ml of 1 X PBS. The fixing solution is removed by flicking the plate in a sink. The plate is then washed once with 0.02% PBS-Tween (Kirkegaard & Perry) using a volume of 250 ul/well delivered with a Cornwall syringe. The plate is again cleared of solution by flicking in a sink.

The wells are subsequently blocked with 100 mM glycine containing 1% BSA at a volume of 100 ul/well for 1 hour. A volume of 10 ml/plate is required for the 100 mM glycine/1% BSA solution which is made by mixing 3.75 g glycine with 5.0 g of BSA in a volume of 500 ml of PBS. This stock is then filtered through a 0.45 micron filter and is kept refrigerated. Blank wells should be left empty. The plate is again flicked in a sink to remove the blocking solution and is washed once with 0.02% PBS-Tween using a volume of 250 ul/well. The PBS-Tween solution (250 ml/plate) is made fresh each time by adding 12.5 ml of a Kirkegaard & Perry 20 X concentrate of PBS-Tween 20 to 237.5 ml of distilled $H_2O$.

Finally, a blocking solution composed of RPMI and 20% FBS is delivered at a volume of 200 ul/well and allowed to remain in contact with each well for 1 hour. The RPMI containing 20% FBS (20 ml/plate) is made fresh each time by mixing 16 ml of RPMI medium with 4 ml of FBS. All blank wells should be left empty. After blocking in this manner, the plates are again cleared by flicking the plate in a sink.

Hybridoma supernatants or patient serum are then added at a volume of 50-100 ul/well and allowed to remain for 1 hour. A positive control of human serum is made fresh each time by diluting to appropriate concentrations with RPMI/20% FBS. For negative controls, wells are loaded with RPMI/20% FBS and blank wells are left empty. Prior to adding antibody, the plate is cleared by flicking in a sink and is washed once with 0.02% PBS-Tween with a volume of 250 ul/well.

A 1:400 dilution of Peroxidase-Labeled Goat Anti-Human Total Ig antibody (Kirkegaard & Perry) is then added using a volume of 50 ul/well and is allowed to remain in contact for 1 hour. Blank wells should be left empty. Peroxidase labeled Goat Anti-Human Total Ig (5 ml/plate) is made fresh each time and is stored at −70° C. in 1 ml aliquots of a 1:100 concentration in PBS containing 1% BSA. A single vial (0.5 mg) of Peroxidase Labeled Goat Anti-Human Total Ig (Kirkegaard & Perry Rehydrate) is mixed with 1 ml of sterile water after which 99 ml of sterile PBS containing 1% BSA is added. A working solution (1:400 concentration) is made conveniently by adding 1.5 ml of the 1:100 stock to 4.5 ml of a solution of RPMI containing 20% FBS. Prior to adding the substrate ELISA adsorption measurements, the plate is cleared in a sink, washed 5 times with 0.02% PBS-Tween using a volume of 250 ul/well each time and the remaining fluid is cleared by flicking the plate in a sink.

A volume of 50 ul of the ABTS substrate (Kirkegaard & Perry) is then added to all wells. The ABTS substrate (5 ml/plate) is made fresh each time by mixing 2.5 ml of Solution A (Kirkegaard & Perry) with 2.5 ml of Solution B (Kirkegaard & Perry) together immediately before using. The plate is then placed in the dark for 30 minutes for color development prior to reading spectrophotometric adsorption results on an ELISA Reader (Bio-Tek Instruments, Winooski, Vt.) at a dual wavelength of 405 and 490 nm.

B and T Cell Separation by AET Rosetting Procedure

A heparinized blood sample is diluted with an equal volume of PBS without calcium or magnesium. A volume of 3 ml of FH 1077 is then added to 15 ml round bottom tubes. A volume of 10 ml of the diluted blood is then added to each tube so that it is layered on top of the FH 1077. The tubes are then centrifuged for 15 minutes at 700-1800 rpm, taking 5 minutes to reach 1800 rpm.

A Pasteur pipet is then used to transfer the interfaces from each tube to a 50 ml centrifuge tube and the interfaces are then washed 2 times with PBS spinning each time at 2000 rpm for 5 minutes. The pellets are resuspended in 10 ml of PBS and a Coulter or hemacytometer count is carried out. At this point, an adherence step (infra) to remove macrophages may be achieved.

Approximately $50 \times 10^6$ cells are added to a 50 ml centrifuge tube along with 5 ml of the AET solution (1 ml per $10 \times 10^6$ cells). This mixture is then centrifuged for 5 minutes at 800 rpm and refrigerated at 4° C. for one hour. The sample is gently resuspended by hand rolling the tube containing the pellet back and forth. Once the cell pellet is resuspended, a drop of sample is removed and placed on a hemacytometer slide and counted for percent rosetting (T cells).

The resuspended cell pellet is then pipetted onto 3 ml of FH 1077 in a 15 ml round bottom tube and centrifuged for 15 minutes at 700-1800 rpm, taking 5 minutes to reach 1800 rpm. The interface (B cells) is removed with a Pasteur pipet and a one drop sample is placed on a hemacytometer slide and counted for the percent of T cell rosette contamination.

The interfaces are then washed 2 times with PBS spinning each time at 2000 rpm for 5 minutes. A drop of the resuspended pellet is placed in a snap cap tube and a drop of the AET solution is added. This mixture is then refrigerated for one hour and checked for percent T cell contamination by counting rosetted cells.

AET Preparation Procedure:

The AET (2-aminoethylisothiouronium bromide; Sigma A 5879, Sigma Chemical Co., St. Louis, Mo.)

solution is prepared by washing 15 ml of sheep red blood cells in Alsever's solution (University of Texas System Cancer Center, Bastrop, Tex.) with PBS lacking both calcium and magnesium. Three washes are accomplished by spinning at 2000 rpm for 10 minutes each time.

Approximately 0.8 g of AET is then added to 7.5 ml distilled $H_2O$ and the solution is brought to a pH of 8.2 with 10N NaOH and the final volume is brought to 10 ml with distilled $H_2O$. The resulting solution is then filtered through a 0.2 micron disc filter attached to a 10 cc syringe into 2.5 ml of packed sheep red blood cells. These treated cells are then placed in a 37° C. waterbath for 20 minutes. The cells are washed 3 times in PBS without calcium or magnesium by spinning at 2000 rpm for 5 minutes.

A 1% solution with RPMI containing 5% FCS is then made by mixing 1 ml of the packed sheep red blood cells in 99 ml of RPMI containing 5% FCS. This preparation may be stored at 4° C. for up to 7 days and is used at a concentration of 1 ml per $10 \times 10^6$ cells.

Macrophage Removal by Adherence Procedure

Tissue culture flasks are coated with FCS and stored overnight in a 37° C. $CO_2$ incubator (loose caps). Volumes of FCS required for variously sized flasks include:

| T-25 flask | 2 ml FCS |
| T-75 flask | 5 ml FCS |
| T-150 flask | 10 ml FCS |

The remaining FCS is then aspirated off.

Whole mononuclear cells are then added to the flasks at a concentration of $2-4 \times 10^6$ cells per ml in RPMI containing 15% FCS. The maximum number of cells per variously sized flask include:

| T-25 flask | $40 \times 10^6$ cells in 10 ml medium |
| T-75 flask | $120 \times 10^6$ cells in 30 ml medium |
| T-150 flask | $240 \times 10^6$ cells in 60 ml medium |

The flasks are then placed in a $CO_2$ incubator at 37° C. for one hour (loose caps). If there are no preconditioned flasks, then cells may be suspended in RPMI containing 20% FCS and allowed to adhere in an incubator for 2 hours.

Using a 10 ml pipet, media is gently washed over the sides of the flasks. The media is then removed along with any suspended cells. The flask should not be scraped. The media and suspended cells are then placed in a 50 ml centrifuge tube and spun at 2000 rpm for 10 minutes. The supernatant is aspirated off and the pellet is resuspended in PBS without calcium or magnesium and a Coulter or hemacytometer count is achieved. Macrophages (adherent cells) may be removed from flasks by refrigerating for one hour and then washing with PBS.

Cell Binding Assays (to Screen Hybridoma Supernatant for Cell Surface Binding Antibodies)

The following assays may be used to screen sera initially for serum reactivity to cell surface structures on ovarian and non-ovarian target cells.

1. Fluorescence Activated Cell Sorter Analysis (FACS Analysis) of Surface Binding Antibody:

Sera from ovarian patients (allogeneic and autologous) may be examined in the fluorescent activated cell sorter (FACS) for reactivity against other non-ovarian tumors and nylon wool purified T cells as control.

Approximately $0.5-1.0 \times 10^6$ cells are washed in HBSS containing 0.2% $NaN_3$ and resuspended (in 50 ul) of this solution. Approximately 0.2-0.5 mg in 50 ul of the appropriate control monoclonal antibody and 50 ul of 1/20 dilutions of the sera to be tested are added to the cells and these then are incubated on ice for 30 minutes. The cells are then washed three times with HBSS and incubated for an additional 30 minutes with the appropriate amount of fluorescein conjugated $F(ab)_2$-fragment of antihuman, mouse, or rabbit chosen according to the nature of the primary antibody. The cells are then washed three times in HBSS, resuspended in the same medium and analyzed by FACS using a log amplifier.

2. Enzyme Linked Immunoabsorption Assay (ELISA).

Approximately $15 \times 10^3$ of target cells are seeded into 96 well microplates (Costar) and incubated for 48 hours at 37° C. Cells are fixed with 10% neutral buffered formalin in PBS (5 minutes at room temperature) and further washed with PBS.

Endogenous peroxidase is blocked by incubating the cells with 100 mM glycine containing 1% BSA for one hour at room temperature. Non-specific binding is blocked with 20% FCS in RPMI 1640 medium. Approximately 50 ul of decomplemented serum or supernatant is added to each well and incubated at 37° C. for one hour. After extensive washing with PBS/Tween 20, (PBS, 0.02% Tween 20), 50 ul of peroxidase conjugated goat antihuman immunoglobulins (Kirkegaard and Perry) are added at 1:400 dilution in 20% FCS in RPMI 1640 and incubated for 1 hour at room temperature. The plates are washed and 50 ul/well of substrate solution is added. Optical density is read at 405 and 490 nm in an ELISA autoreader (Biotek) after 30 minutes incubation at room temperature.

3. Mixed Hemadsorption Assays (MHA) and Staphylococcal Protein A Assays (SPSA).

Approximately $15 \times 10^3$ target cells are plated into wells of 96 well tissue culture microplates (Costar). After 48 hours of incubation at 37° C., plates are washed and supernatants are added to each well. Indicator cells are prepared by conjugating staphylococcal protein A (Pharmacia Fine Chemicals, Uppsala, Sweden) or goat antihuman antibodies (Cappel) to human group 0 Rh+ erythrocytes with 0.01% $CrCl_3$ (pH 5). After 1 hour incubation with diluted sera, plates are washed and exposed to a 0.2% suspension of indicator cells for one additional hour. Plates are then washed to remove unattached red blood cells. Approximately 200 tumor cells are counted per well, and the wells are designated positive when 2 or more erythrocytes are attached to more than 10% of the target cells. The following assays may be used to demonstrate microscopically the site of human monoclonal antibody binding (these assays may be performed with positive supernatant on selected tumor cells):

1. Surface Binding Indirect Immunofluorescence (nonpermeabilized).

Surface binding indirect immunofluorescence of nonpermeabilized cells is accomplished as previously described (infra).

2. Intracellular Binding Assays a. Indirect Immunofluorescence on Permeabilized Cells.

The procedure for indirect immunofluorescence on permeabilized cells is the same as for non-permeabilized cells except that cells are fixed with 3.5% formaldehyde for 30 minutes at room temperature and permeabilized by incubation with 0.5% Nonidet P40 (Sigma Chemical Co., St. Louis, Mo.) in PBS containing 0.02% for $NaN_3$ 10 minutes at room temperature prior to the addition of antibodies.

b. Indirect Immunoperoxidase on Fixed Cells.

Cells are harvested in the exponential growth phase. Cryostat sections of tumor tissues are fixed with acetone for 10 minutes at 4° C. and further washed with PBS. Acetone obviates the need for quenching to account for endogenous peroxidase. Fixed cultured cells and tumor sections are incubated with 20% diluted normal goat serum for 30 minutes after which goat serum is removed and the slides are washed with PBS. The preparations are then incubated for 1 hour with test antibody at room temperature.

After further washing, cells are incubated for 1 hour with biotinylated antihuman antibody (Vector Labs, Burlingame, Calif.). Slides are washed and avidin DH biotinylated horseradish peroxidase H complex (Vector Lab.) is added for 30 minutes. After another rinse with PBS, slides are treated with 3-amino-9-ethyl-carbasole (Biogenex Lab, Dublin, Calif.) for 10–20 minutes at room temperature. Preparations are again rinsed with PBS, counterstained with Gill's hematoxylin (Poly-Sciences, Inc., Warrington, Pa.) and mounted with Aqua Poly Mount (Poly-Sciences).

Determination of Competing Monooclonal Antibodies as a Method for Identifying Further Useful Monoclonal Antibodies The following procedure demonstrates a method for determining the degree of similarity of epitopic specificity as between a monoclonal antibody of unknown specificity and a reference monoclonal antibody of a defined specificity possessing certain desired characteristics such as cell surface binding of gynecological tumor cells.

This assay takes advantage of a double antibody assay where a capture and a probe antibody are used in combination to bind a specific antigen on the surface of a gynecological tumor cell. In this assay, the binding of a known capture/probe antibody combination with a known antigen is compared in the presence or absence of a relative excess of a third antibody having an unknown epitopic specificity.

Thus, when the unknown antibody has a similar epitopic specificity as the capture antibody, the amount of antigen available for binding to the matrix-bound capture antibody is reduced. Alternatively, if the unknown antibody has a specificity that is similar to that of the probe antibody, the binding of the labeled probe to the capture-antigen complex is correspondingly reduced. In either case, when the antibody successfully competes, the absorbance obtained is reduced or eliminated relative to a control assay without the unknown antibody.

COMPLEMENT MEDIATED CYTOTOXICITY ASSAY

The complement mediated cytotoxicity of AC6C3 is tested by a cell lysis assay. MDAH2774 cells are grown until they exhibit 70–90% confluent growth, the cells are separated from the culture medium and washed once with PBS by swirling in the culture-flask. The PBS wash is discarded and the cells are scraped gently from the flask walls into 10 ml of fresh PBS. The cells are quantitated and checked for viability.

Where viability is determined to be less than 50%, dead cells are removed by the Ficoll-Hypaque method. That method involves reconstituting the cells with 2 ml of minimal essential medium (MEM; GIBCO) and 0.2 ml of Ficoll-Hypaque ($1-2 \times 10^6$ cells per 2 ml of Ficoll mixture). The cells are then mixed in the solution and allowed to stand for five minutes. The suspended cells are next layered on to Ficoll-Hypaque solution (supra) and centrifuged for 15–20 minutes at 1,200 RPM (if no cells are seen at the bottom of the test tube, the tube is re-centrifuged for 10 minutes at 1,500 RPM). Finally, the live cell fraction is washed twice with MEM.

After a known quantity of viable cells is obtained at a viability of greater than 90%, approximately 200,000 of such cells are placed in each of six test tubes. The supernatant is removed from the cells and 200 ul of test medium are added as follows:

| Test Tube No. | First Incubation | Second Incubation |
|---|---|---|
| 1 | 2774 + HM | + HM |
| 2 | 2774 + HM | + Complement |
| 3 | 2774 + AC6C3 S/N | + HM |
| 4 | 2774 + AC6C3 S/N | + Complement |
| 5 | 2774 + ASC G1 3174 1/100 | + HM |
| 6 | 2774 + ASC G1 3174 1/100 | + Complement |

Where 2774 represents the 200,000 MDAH2274 cells, HM represents hybridoma medium, AC6C3 S/N represents supernatant containing anti-ovarian monoclonal antibody derived from the hybridoma AC6C3, ASC G1 3174 1/100 represents a 1:100 dilution of a mouse serum antibody known to exhibit complement-mediated cytotoxicity, and where complement is human-derived blood complement protein.

The test solutions are incubated for two hours at 4° C. then washed once with MEM and resuspended with 200 ul of HM. Next, 20 ul of low-toxicity, rabbit complement H2 are added to test tubes 2, 4 and 6 and all tubes are incubated at 37° C. for 30 minutes.

At the end of the incubation period, the cells are again checked for viability. If the viability is greater than 80%, further cycles of additional rabbit complement H2 and incubation is achieved until cell viability is below 20%.

TREATMENT PROTOCOLS

Cytotoxic Treatment

The following treatment protocol for use of the monoclonal antibodies of the invention is derived from a protocol for adjunctive intralymphatic immunotherapy with viral oncolysate in high risk patients with uterine cervical cancer. It is disclosed here for the purposes of identifying a preferred approach to such treatment.

Initially, a complete history and physical exam of the patient to be treated with monoclonal antibody of this invention is achieved, including a documentation of all measurable disease as represented diagrammatically in the patient's chart. Laboratory studies should include CBC, platelet count, differential, urinalysis, SMA-12, BUN, creatinine, bilirubin, SGOT, alkaline phosphatase, albumin, total protein, calcium, phosphate, antinuclear factor screen, lymphocyte subset analysis and $TA_4$ tumor marker. Additionally, skin test reactions to three standard recall antigens (dematophytin, candida and mumps), PR8 virus antigen, and a panel of coated unmodified tumor antigen extracts will be preformed prior to the treatment.

Patients will receive a monoclonal antibody dose at a dose level determined in phase I trials. Subsequent dosings of this patient will be determined by optimum stimulation patterns without an unacceptable toxicity. The antibody will be injected into dorsal lymphatics of each foot at −28 days and −14 days prior to initiation of radiation). The intervals between interlymphatic procedures may need to be lengthened for subsequent treatments if edema precludes performance of the cutdown procedures. In general the procedure is identical to that performed for lymphangiographic purposes.

The monoclonal antibody will be injected under gravity, with each injection to be completed within 30 minutes. The feet will be checked for infection or inflammation before each procedure.

Radiation therapy, if so desired, will commence between days −7 and 0 and will be delivered as follows. Standard radiation therapy will be administered as a high energy photon beam to a dose of 4500 rads at 180 rads/fraction to include an extended field 4 cm above the highest detected node involvement, with or without a boost to nodes. This will be followed by two radium systems which will deliver between 4500 and 6500 mg hrs. Additional boosts to the uninvolved nodes may be given at the discretion of the patient's physician. Boosts to involved nodes will use 18–25 Mev photons, preferably, and will be treated with a maximum daily dose of 200 rads/day for a maximum combined tumor dose of 6000 rads. Transvaginal cone irradiation may be permitted before or during the antibody treatment if medically indicated.

Patients undergoing such treatment will receive repeat clinical and pelvic examinations, KUB, and chest x-rays prior to commencing any irradiation and thereafter at 3 monthly intervals for the first year. A chest x-ray will be done at 4 monthly intervals during the second year. The KUB should permit evaluation of response to the treatment before commencement of radiation and CT scan of the abdomen will be repeated every 6 months.

A complete response will be indicated by complete disappearance of the primary tumor, and clearance of the abnormality in the lymph nodes without the appearance of new lesions at any site. Partial response will be indicated by a 50% or more decrease in the tumor volume, with or without persistence of node abnormalities for at least 8 weeks. A partial response will also be indicated if nodal abnormalities persist in the presence of complete regression of the primary lesion, especially if persistent disease is documented by other methods, e.g., CT scan or biopsy. A notation will be made on regression of nodal metastases prior to the institution of radiation therapy. A minimum response is indicated by a decrease in the tumor measurements which are insufficient to qualify for a partial response. No change is indicated by absence of progression for a period of 8 weeks from the completion of radiation therapy. A 25% or greater increase in any measurable tumor parameter will be indicative of an increasing disease state. The antibody may also be administered to patients with recurrent cancer. In other situations (e.g., ovarian cancer), the antibody will be labeled with an isotope or plant toxin and injected intraperitoneally, intravenously, or both in a patient with ovarian cancer on one or more occasions. In other situations, the antibody may be used in conjunction with complement to achieve complement-dependant cytotoxicity.

In Vitro Imaging

The following diagnostic protocol for use of the monoclonal antibodies of the invention in an in vitro imaging procedure is derived from a protocol for radiolocalization following intraperitoneal administration of monoclonal antibodies to ovarian carcinoma patients. It is disclosed here for the purposes of identifying a preferred approach to such diagnoses.

Approximately 7 days prior to surgery, the patient will receive a dose of $^{131}$I-labeled monoclonal antibody. Patients will be scanned with a gamma camera at approximately 2 hours post antibody administration and daily thereafter until surgery is performed. At surgery, suspected carcinoma lesions and selected normal tissues will be removed. Specimens from all biopsies will be immediately weighed and placed in a gamma counter to determine the number of cpm/gram. Tissues should then be examined by routine pathological processing and examination. Fixed biopsy specimens are analyzed for percentage of tumor cells of total cells present and for antigen positive cells using the monoclonal antibodies and the immunostaining procedures of the invention. The location of the reactive antigen (i.e., intracellular, membrane associated, and/or extracellular) is also to be noted.

More specifically, patients will receive a single dose (as determined previously) of purified IgM. The amount of $^{131}$I per mg of antibody will range from 0.30 to 12.48 mCu. Serial gamma camera whole body images and whole body gamma counts will be obtained immediately after the infusion of the monoclonal antibody between 3 and 7 days prior to surgery. Positive areas of uptake will be charted for the surgical sampling. In addition, correlative imaging such as liver, spleen scans or blood pool imaging with $^{99m}$Tc-human serum albumin may be performed to clarify questionable areas and in order to improve detection.

Patients are expected to undergo exploratory laparotomy 5 to 14 days after antibody administration as part of their standard clinical managements. Careful documentation will be made of the location and size of metastatic deposits for correlation with gamma scanning. As much tumor tissue as possible should be removed consistent with standard clinical management and will be labeled to indicate the site of the involvement. Attempts should be made to remove a tumor or to biopsy all sites that show uptake on gamma images. Additionally, small (approximately 1 gram) biopsies should be taken of various normal tissues including omentum, peritoneum, rectus muscle and liver, if possible. Samples of peritoneal fluid will also be obtained for cytology and gamma counting.

A radio localization index (RI) may be utilized and is defined by the formula:

$$RI = \frac{cpm/g \text{ tumor tissue}}{cpm/g \text{ normal tissue}}$$

Normal tissue will be defined for each patient as the average "cpm/g" from biopsies of normal tissues which will include the omentum, peritoneum and liver. All tissue will be weighed and counted in a gamma counter and then confirmed pathologically to be tumor, normal or mixed. If a tissue specimen is found to contain less than 20% tumor it will not be analyzed.

The percent of injected radioactivity that is taken up by one gram of tumor can be calculated as follows:

$$\text{percentage injected dose per gram of tumor isotope} = \frac{cpm/g \text{ tumor}}{\text{total } cpm \text{ of injected (corrected for decay)}}$$

The monoclonal antibody of the invention which provides the best localization will be determined for each patient based on the RI's as follows. Monoclonal antibodies will be combined in pairs by means of simultaneous administration of the pair of monoclonal antibodies radiolabeled with $I^{125}$ (A) versus $I^{131}$ (B). Radionuclide A vs. radionuclide B will be compared by simultaneous administration of these radionuclides each coupled to approximately 1 ml each of the same monoclonal antibody. The RI will be determined for each biopsy site for each radionuclide. Biopsies that contain less than 20% malignancies will not be used for further evaluation for paired monoclonal antibodies or for paired radionuclides. Biopsy specimens that do not show a positive RI (that is, greater than or equal to 3) for either of the radionuclides will not be used for evaluation of the paired monoclonal antibodies or paired radionuclides. The mean of the ratio of the RI's for both monoclonal antibodies or both radionuclides will be calculated over the remaining malignant biopsies as well as two sided 95% confidence intervals for the ratio.

The examples which follow are believed to constitute a thorough disclosure of the preferred embodiments of the invention, and further exemplify the surprising and unexpected nature of various aspects of the invention. One of the examples discloses the less preferred approach of obtaining a cell surface specific monoclonal antibody without pre-treatment with viral oncolysate. The other example illustrates the unique advantages of pre-treatment with viral oncolysate.

It will be appreciated that the modes of practice employed in the following examples are founded on laboratory techniques preferred by the present inventors. Thus, it will be apparent to those of skill in the art, in light of the present disclosure, that numerous other embodiments may be practiced without departing from the spirit and scope of the invention.

EXAMPLE I

Production of the CR Hybridoma Cell Line

This fusion (CR) was produced using peripheral blood of a patient immunized with viral oncolysate. The viral oncolysate used was an extract of the SW756 cervical carcinoma cell line which had been artificially infected with a Puerto Rican strain of influenza A. A volume of 30 ml of peripheral blood was obtained from the patient 7 days after the second intralymphatic VO injection. Lymphocytes were separated by Ficoll-Hypaque density gradient and fused as described supra. Of the 486 seeded wells, 215 (44%) showed growth. Of these 215 wells, 36 were positive by ELISA and 1 demonstrated surface binding antibody reactivity with the SW756 cell line. The CR4E8E10 hybridoma has been deposited with the American Type Culture Collection and designated HB 10304. Further, the cell line SW756 has been deposited with American Type Culture Collection and afforded ATCC designation No. CRL 10302. The hybridoma was cloned on 1 occasion and 76 ELISA positive wells were obtained, 74 of which had surface antibody binding by microscopic immunofluorescence. The antibody was subtyped as an IgM.

Figure 1B:
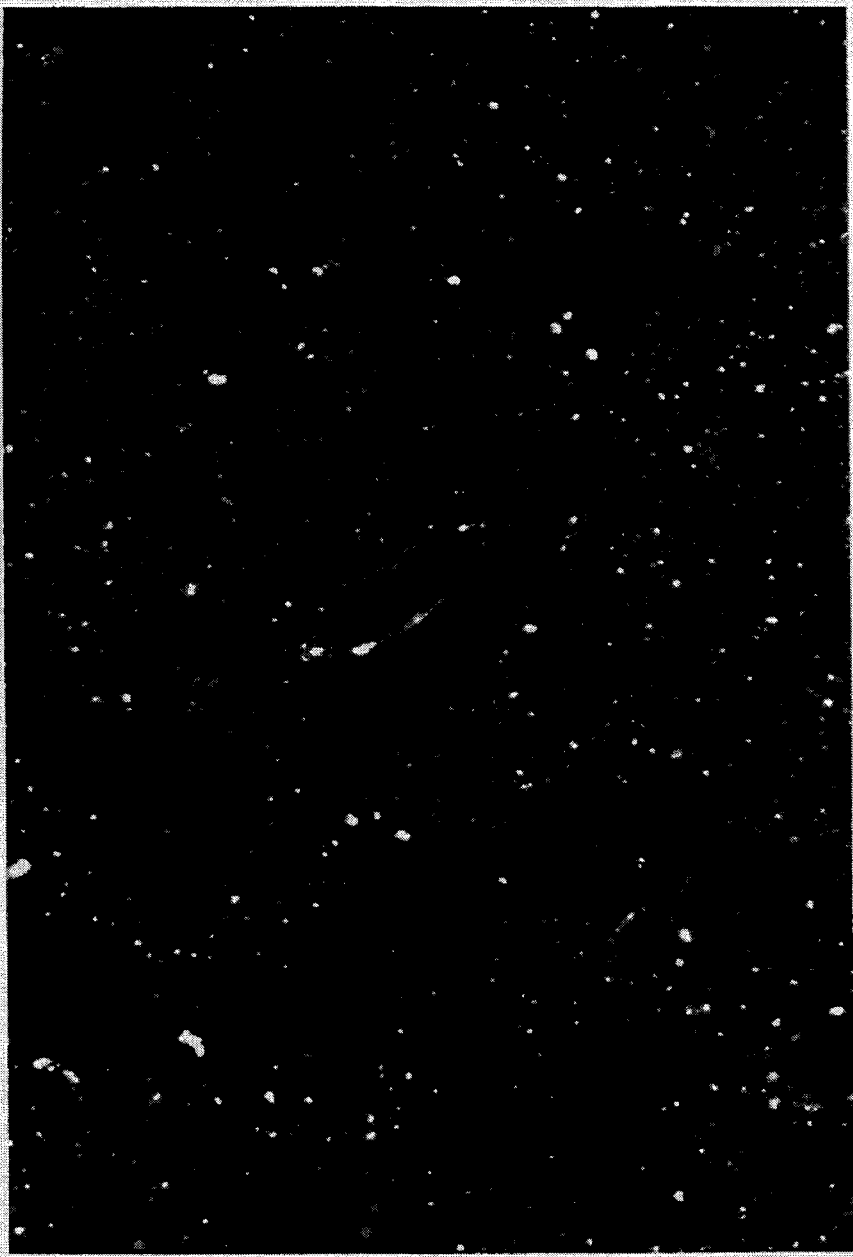
FIG. 1B. Immunofluorescence Assay. Fluorescence microscopy of SW756 cells treated with CR (4E8E10) hybridoma supernatant.

FIGS. 1A and 1B demonstrate the utility of the CR hybridoma supernatant in an immunofluorescence assay of the cervical carcinoma cell line SW756. Cells of SW756 were treated via the methods of the invention and exposed to the CR hybridoma supernatant (clone 4ESE10). The immunocomplexed cells were then viewed alternatively by brightfield (FIG. 1A) or fluorescence microscopy (FIG. 1B).

Fluorescence activated cell sorter analysis data is shown for the CR subclone CR4E8E10E10 as against cells from a variety of tumor sources (Table 1). Similarly, immunofluorescence data is summarized for the mother cell line CR4E8 and several of its subclones as against an array of tumor cell lines (Table 2).

TABLE 1

Reactivity of Human Anti-Cervix Surface Reacting Monoclonal Antibody CR4E8E10E10 with Cervix Carcinoma and Non-cervix Carcinoma Cell Lines by Immunofluorescence (FACS)

| Cell Line Source | Cell Lines Tested | % Positive Cells[2] April–June/89 | Oct/89 |
|---|---|---|---|
| Cervical Squamous | SW756 | 13, 20, 21, 21 | 82 |
|  | 431 | 29 61 |  |
| Vulvar Squamous | 962 | 37 | 11, 42 |
| Ovarian Epithelial | 2774 | 14, 23 | 39 |
|  | CaOV3 | 10, 31 | 37 |
|  | SKOV3 | 28 | 43 |
|  | GB |  | 17, 51 |
| Colon | SW48 | 31 | 66 |
|  | SW480 | 12 | 75 |
| Breast | MD435 | 14 | 32 |
|  | MD436 | 24 | 48 |
| Fibroblast | MRC-5 | 17, 83 | 55 |
| Melanoma | A375 | 7 9 | 54 |
| Sarcoma | SK-UT-1[1] | 11 | 55 |
| Hematopoietic | K562 | 8 |  |
|  | Daudi | 1 | 12 |
|  | Jurkatt | 17 | 25 |

[1]Cytologic features suggest adenocarcinoma
[2]Each cell line was used as its own control and the reactivity was uniformly found to be less than 5%.

TABLE 2

IMMUNOFLUORESCENCE DATA - CR4E8

| DATE | OR CLONE | CELL LINE SW756 | SK-UT-1 | A375 | CaOV3 | 2774 | SKOV3 | 962 | MRC-5 |
|---|---|---|---|---|---|---|---|---|---|
| 9/29/88 | CR4E8 | +++ |  |  |  |  |  |  |  |
| 11/11/88 | CR4E8E10 | +++++ |  |  |  |  |  |  |  |
|  |  |  |  |  | Thawed 11/23/88 |  |  |  |  |
| 12/22/88 | CR4E8E10 | +++ |  |  |  |  |  |  |  |
| 1/12/89 | CR4E8E10 | +++ | + | ++ | − | ++ | ++ | ++ | + |
|  |  |  |  |  | Thawed 01/13/89 |  |  |  |  |
| 2/9/89 | CR4E8 E10E10 | ++ |  |  |  |  |  |  |  |
| 3/9/89 | CR4E8 E10E10 | + |  |  |  |  |  |  |  |
| 4/6/89 | CR4E8 | ++ |  |  |  |  |  |  |  |

TABLE 2-continued

| | | IMMUNOFLUORESCENCE DATA - CR4E8 | | | | | | | |
|---|---|---|---|---|---|---|---|---|---|
| | | CELL LINE | | | | | | | |
| DATE | OR CLONE | SW756 | SK-UT-1 | A375 | CaOV$_3$ | 2774 | SKOV$_3$ | 962 | MRC-5 |
| | E10E10 | | | | Thawed 06/02/89 | | | | |
| 6/22/89 | CR4E8 E10E10 | +++ | | | | | | | |

CODE:
SW756 Squamous Carcinoma Cervix
SW962 Squamous Carcinoma Vulva
CaOV3
2774 Epithelial Carcinoma Ovary
SKOV3
SKUT-1 Sarcoma Uterus
A375 Melanoma
MRC5 Fetal Fibroblast

EXAMPLE II

Production of the AC Hybridoma Cell Line

Cells were obtained from the lymph node of this patient who was found to have a stage I, grade 1 mucinous carcinoma of the ovary. The lymph node was taken to the laboratory under sterile conditions, minced and suspended in RPMI 1640. Fusion was performed with SPAZ 4 at a cell ratio of 1:1 with PEG 1500 added, followed by wash medium containing Versene and RPMI. The cells were then suspended in HT medium which included Iscoves with 20% fetal calf serum, 5 ug/ml insulin, 5 ug/ml transferrin, NCTC 109 medium 10%, and hypoxanthine 13.6 ug/ml, thymidine 7.7 ug/ml and glycine 0.5 ug/ml at a concentration of $1 \times 10^6$ cells/ml and plated at 0.1 ml/well. Then, 382 wells were seeded in 96 well microtiter plates.

The results of the fusion are summarized in Table 3. The hybridoma growth rate was 86% of the total number of wells plated and on day 7 there were 25 clones/$1 \times 10^6$ cells originally fused. Supernatants from the growing wells were tested in a standardized ELISA assay using goat anti-human total immunoglobulin (Cappel). Approximately, 145 of the 331 wells (44%) showing growth were positive by ELISA assay. Wells showing the highest ELISA readings were tested by indirect immunofluorescence for binding on ovarian tumor cell lines. Nine supernatants were found to have positive fluorescence against 2 cultured and characterized ovarian carcinoma cell lines, CaOV$_3$ and MDAH 2774. The hybridomas were cloned by limiting dilution on irradiated mouse thymocytes derived from pathogen free Balb/C mice and retested for immunoglobulin production. Clonings were resolved by 9/30/88, and Ig isotype analysis (heavy and light chains) in a standardized ELISA assay indicated that both clones were IgM producing.

Antibody reactivity with cultured carcinoma cell targets has been demonstrated using a standardized indirect immunoperoxidase technique after acetone fixation of target cell preparations. A non-reactive human monoclonal antibody was used as a negative first antibody control. Short term tumor cell cultures from AC's tumor also demonstrate positive reactivity by the immunoperoxidase technique.

The utility of the AC cell line in diagnostic techniques was demonstrated by applying the immunofluorescence techniques (FIGS. 2A and B) or immunoperoxidase techniques (FIGS. 3A, B, C) of the invention to tumor cells.

Figure 2A:
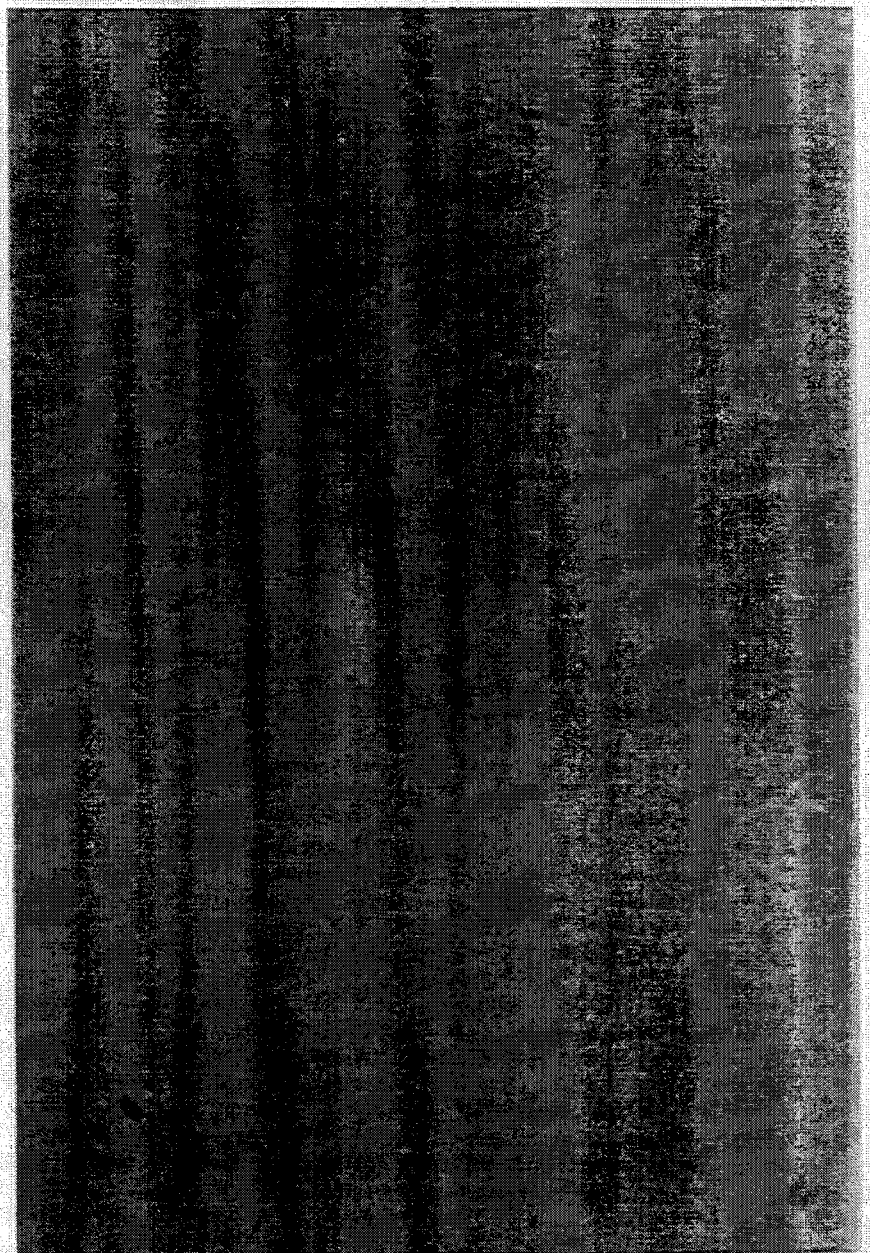
FIG. 2A. Immunofluorescence Assay. Brightfield microscopy of CaOV$_3$ cells treated with AC (6C3) hybridoma supernantant.
Figure 2B:
FIG. 2B. Immunofluorescence Assay. Fluorescence microscopy of CaOV$_3$ cells treated with AC (6C3) hybridoma supernantant.

FIGS. 2A and 2B demonstrate the use of AC hybridoma supernatant (clone AC6C3) in a immunofluorescence assay of the ovarian carcinoma cell line CaOV$_3$. Cells of CaOV$_3$ were treated via the methods of the invention and exposed to the AC hybridoma supernatant. The immunocomplexed cells were then analyzed using, alternatively, bright field (FIGS. 2A) or fluorescence microscopy (FIG. 2B).

Figure 3A:
FIG. 3A. Immunofluorescence Assay. H & E staining of cells from patient #233269.
Figure 3B:
FIG. 3B. Immunoperoxidase Assay. Cells of patient #233269 treated similarly to those in C below, except that a non-reactive supernatant is used.
Figure 3C:
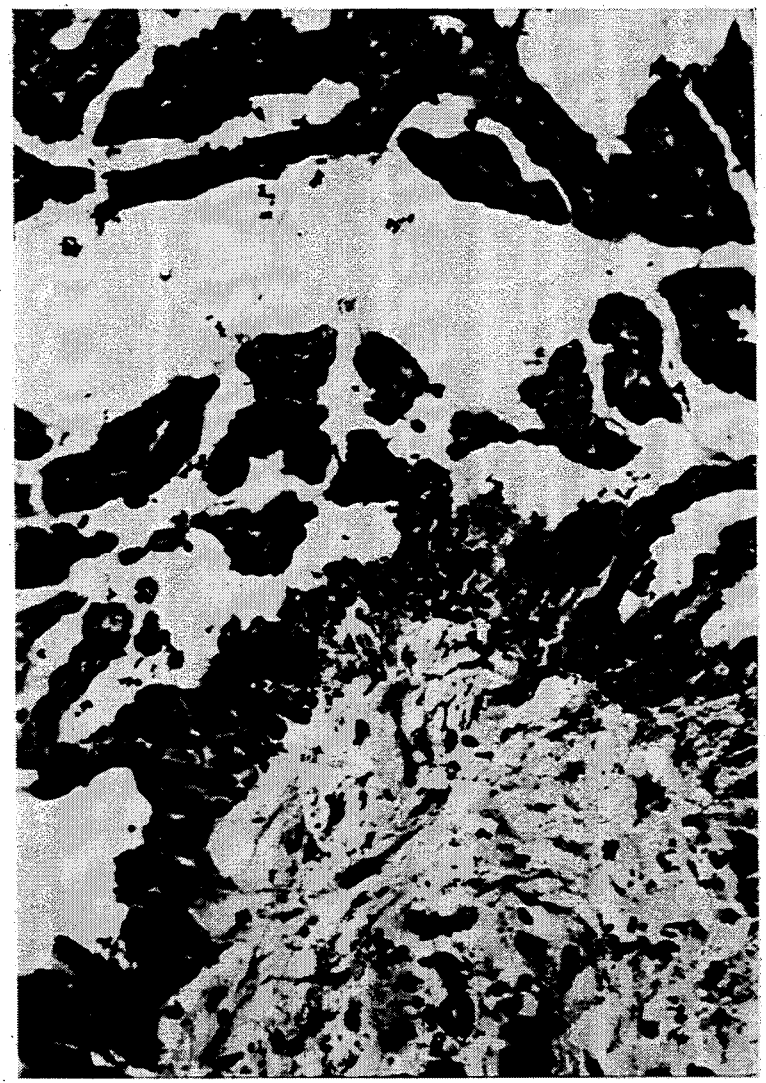
FIG. 3C. Immunoperoxidase Assay. Cells of patient #233269 treated with AC (6C3) hybridoma supernatant.

Similarly, the AC hybridoma was used in the immunoperoxidase techniques of the invention to selectively stain ovarian cancer cells of a particular patient (FIGS. 3A, B, C). The hybridoma AC6C3 has been deposited with the American Type Culture Collection (located in Rockville Md.) on Dec. 6, 1989, and was designated HB 10305 by that depository. Further, the cell line MDHA 2774 has been deposited with American Type Culture Collection and designated CRL 10303. FIGS. 3A and B represent staining of ovarian tumor cells of a patient with either hematoxylin and eosin stain (Fisher Scientific, Houston, Tex.) (FIG. 3A) or with a non-reactive supernatant (FIG. 3B). These same cells when treated with the ovarian hybridoma supernatant, AC, stain brown (FIG. 3C).

The antibody demonstrated strong surface binding reactivity by immunofluorescence against CaOV$_3$ and MDAH 2774. Fluorescence activated cell sorter analysis (FACS) data is shown for several subclones (Tables 4 and 5). 7D2 is a partially cloned hybridoma producing IgA and M. AC6C3 has been cloned and is now identified as D1 and E11. Doubling times were 24 hrs for AC6C3D1 and 32 hrs for AC6C3E11. Immunoglobulin production is respectively, 1.5 and 3 ug/ml for $10^6$ cells measured at 24 hrs for D1 and E11.

TABLE 3

| | LYMPHOCYTE FUNCTIONS | | | | | |
|---|---|---|---|---|---|---|
| | | | Lymphocyte source | | | |
| | Peripheral Blood Lymphocytes | | Lymph Nodes | | | Bone Marrow |
| | Tumor Type | | | | | |
| | Ovary | Cervix | Ovary | Sarcoma | Vulva | Ovary |
| Sample Number Immortalization Procedure | 16 | 7 | 10 | 2 | 1 | 1 |

TABLE 3-continued

| | LYMPHOCYTE FUNCTIONS | | | | | |
|---|---|---|---|---|---|---|
| | Lymphocyte source | | | | | |
| | Peripheral Blood Lymphocytes | | Lymph Nodes | | | Bone Marrow |
| | | | Tumor Type | | | |
| | Ovary | Cervix | Ovary | Sarcoma | Vulva | Ovary |
| 1. Direct fusion | — | — | 9 | 2 | 1 | — |
| 2. In vivo activation + Fusion | 8 | 7 | — | — | — | — |
| 3. In vivo activation + Fusion | 5 | — | 1 | — | — | 1 |
| 4. EBV + Fusion | 3(1C) | — | — | — | — | — |
| % wells with growing hybridomas | | | | | | |
| 1. Range | 0–59.7 | 19.4–53.2 | 0–88.7 | 52.7,88.9 | 84.5 | 0 |
| 2. Median | 2.1 | 44.2 | 20.2 | N/A | N/A | — |
| Fusion Frequency | 0–18.6 | 8.85–22.0 | 0–25.0 | 29.0,30.0 | 27.0 | 0 |
| 1. Range | 3.1 | 13.5 | 11.0 | N/A | N/A | — |
| % Ig Producing from growing Hybridomas | | | | | | |
| 1. Range | 0–95.2 | 15.0–84.0 | 7.1–100 | 15.5,21.5 | 49.1 | — |
| 2. Median | 10.9 | 24.7 | 13.1 | N/A | N/A | — |
| No. of fusions producing surface tumor Reactive Ab | 2 | 2• | 20 | 2** | 1** | — |

Fusion Frequency = # of colonies × $10^6$ lymphs
1C = one contaminated sample
* = two samples incomplete
= both followed in vivo vaccination with IP VO but hybridoma did not survive
• = both followed in vivo vaccination with intralymphatic VO, one growing successfully (CR)
= one successfully growing (AC)
** = no surviving hybridomas

TABLE 4

Reactivity of HuMoAb with CaOv3 Ovarian Cell Line

| | % Positive cells in the areas | |
|---|---|---|
| Sample | 1+ | 3+ |
| Negative Control | 3.2 | — |
| AB Serum | 27.2 | 2.8 |
| Positive Control | 95.5 | 91.2 |
| 5E9 | 55.5 | 28.6 |
| 6C3 | 72.1 | 60.6 |
| 6E9 | 48.8 | 12.6 |
| 7D2 | 75.3 | 66.2 |
| 6F11 | 71.7 | 57.6 |

CaOv3 cells were grown in standard culture conditions. Cells were removed from cultures by gentle scraping, washed and incubated with 50 ml culture supernatant from hybridoma growing wells for 30 min. at 4° C. After the cells were washed and incubated with 1/40 dilution of antihuman total immunoglobulin - FITC conjugated antibody (TAGO). After additional 30 min. of incubation, the cells were washed, resuspended in PBS and examined with an EPICS ® - Profile Analyzer (Coulter Corporation) with the log amplifier.
Negative control: CaOv3 cells incubated only with the FITC conjugated antibody; AB serum: CaOv3 cells were incubated with 1/20 dilution of heat inactivated pooled human AB serum; Positive control: Serum from a patient receiving viral oncolysate therapy with a CaOv3 derived vaccine, and known to have developed antibodies reacting with CaOv3 cells.
Background reactivity of human AB serum with CaOv3 cells was determined as 27.2%. Reactivity of human hybridoma supernatants with the CaOv3 cells was calculated for both areas (1+ and 3+) to facilitate the evaluation of the HuMoAb reactivity.

TABLE 5

Reactivity of HuMoAb with 3 Ovarian Cell Lines

| HuMoAb Cells Subclone | Tested | % Positive | | | | NW-PBMC* |
|---|---|---|---|---|---|---|
| | | CaOv3 | 2774 | SKOv3 | SKUT-1 | |
| 7D2 | 1 | 32.3 | 76.5 | 24.8 | 12.6 | 0.8 |
| | 2 | 52.3 | 88.3 | 40.2 | 18.9 | 1.2 |
| 6C3 | 1 | 28.8 | 71.3 | 7.8 | 7.1 | 2.2 |
| | 2 | 28.2 | 80.8 | 15.5 | 7.3 | N.D. |
| Negative control | | 6.3 | 14.1 | 3.9 | 1.8 | 1.0 |

*Nylon wool non-adherent autologous peripheral blood monoclonal cells
MDAH 2774, CaOv3 and SKOv3 are three characterized ovarian carcinoma cell lines. SKUT-1 is derived from mixed mesodermal sarcoma of the uterus.

EXAMPLE III

The reactivity of the human anti-ovarian surface reacting monoclonal antibody AC6C3 was tested with ovarian carcinoma cells and with a variety of non-ovarian cell lines using the immunoperoxidase procedures described (supra). The resulting slides were scored using standard pathological analysis and procedures. The relative reactivity found for each cell line is summarized in Table 6.

TABLE 6

Reactivity of Human Anti-Ovarian Surface Reacting Monoclonal Antibody AC6C3 with Ovarian Carcinoma and Non-Ovarian Cell Lines by Immunoperoxidase

| Cell Source | Cell Line | Relative Immunoreactivity[2] |
|---|---|---|
| Ovarian Epithelial | 2774 | ++ |
| | CaOV3 | ++ |
| | SKOV3 | ++ |
| | GB | ++ |
| Cervical Squamous | SW756 | + |
| | A431 | ++ |
| Vulvar Squamous | 962 | + |
| Colon | SW48 | ++ |
| | SW480 | + |
| Fibroblast | MRC-5 | ± |
| Melanoma | A375 | ++ |
| Sarcoma | SK-UT-1[1] | ++ |
| Hematopoietic | K562 | ± |
| | Daudi | ± |

TABLE 6-continued
Reactivity of Human Anti-Ovarian Surface Reacting Monoclonal Antibody AC6C3 with Ovarian Carcinoma and Non-Ovarian Cell Lines by Immunoperoxidase

| Cell Source | Cell Line | Relative Immunoreactivity[2] |
|---|---|---|
| | Jurkatt | − |

[1]Cytologic features suggest adenocarcinoma (ATCC)
[2]Strong (++), moderate (+), weak (±), negative (−)

EXAMPLE IV

The relative reactivity of the human anti-ovarian surface reacting monoclonal antibody AC6C3 was tested on cryostat sections of epithelial ovarian carcinoma specimens and compared to similar sections of other malignant as well as non-malignant tissues using the immunoperoxidase procedures of the invention. The resulting slides were scored using standard pathological analysis and procedures. The relative reactivity found for each tissue section is summarized in Table 7.

In certain cases, and in the kidney tissues in particular, the second antibody used in conjunction with the monoclonal antibody of the invention gave positive results. This was determined by utilizing identical procedures but omitting the monoclonal antibody. These type results are distinguished in the data of Table 7. In the case of certain normal kidney tissues, the site of non-specific reactivity is also indicated.

When the reactivity of human anti-ovarian surface reacting monoclonal antibody AC6C3 is tested by the immunoperoxidase reaction against xenografts of human tumors and cell lines developed from such tumors (SKOV3) and then grown in nude mice by standard methods known to those in the art, immunoreactivity is always present. The American Type Culture Collection accession number of SKOV3 is HTB77. Representative data indicating this fact is shown in Table 8.

TABLE 7
Reactivity of Human Anti-Ovarian Surface Reacting Monoclonal Antibody AC6C3 with Cryostat Sections of Epithelial Ovarian Carcinoma and other Malignant and Normal Tissues by Immunoperoxidase Reaction

| | No. of Patient Specimens | Relative Immunoreactivity[1] |
|---|---|---|
| Malignant Tissues | | |
| Ovarian | 4 | ++ ++ ++ ++ |
| Ovarian Ascites | 3 | ++ ++ ++ |
| Cervix | 1 | + |
| Breast | 2 | ++ ++ |
| Lung | 1 | + |
| Sarcoma | 2 | NS[2] ± |
| Colon | 3 | + ++ ++ |
| Kidney | 1 | − |
| Melanoma | 2 | ± ++ |
| Normal Tissues | | |
| Ovarian | 2 | − − |
| Breast | 1 | + |
| Lung | 2 | NS NS |
| Kidney | 1 | − |
| | 1 | Tubular lumen &[3] blood vessels reactive |
| | 1 | tubule reactive[3] |
| Heart | 1 | NS |
| Peritoneum | 1 | − |

Strong (++), Moderate (+), weak (±), negative (−)
[2]NS = Nonspecific second antibody reaction
[3]Weak reactivity

TABLE 8
Reactivity of Human Anti-ovarian Surface Reacting Monoclonal Antibody AC6C3 with Nude Mouse Human Tumor Xenograft by Immunoperoxidase Reaction

| Specimens | Immunoreactivity[1] |
|---|---|
| WRI N89-20409 NP2 | ++ |
| SMI N89-20416 NP5 | ++ |
| SKOV3 N89-20554 NP1[2] | ++ |
| PAX N89-20571 NP8 | ++ |
| LAN N89-20590 NP4 | ++ |

[1]Strong (++), moderate (+), weak (±), negative (−)
[2]Human ovarian tumor cell line

EXAMPLE V

The relative reactivity of the human anticervix surface reacting monoclonal antibody with cervix carcinoma and other non-cervix cell lines was determined by immunoperoxidase reaction described (supra). The cytospin slides were scored using standard pathological analysis and procedures. The relative immunoreactivity for each cell line is summarized in Table 9.

TABLE 9
Reactivity of Human Anti-Cervix Surface Reacting Monoclonal Antibody with Cervix Carcinoma and other Non-Cervix Cell Lines by Immunoperoxidase Reaction

| Cell Source | Cell Lines Tested | Relative Immunoreactivity[1] |
|---|---|---|
| Cervical Squamous | SW756 | ++ |
| | 431 | ++ |
| Vulvar Squamous | 962 | ++ |
| Ovarian Epithelial | 2774 | ++ |
| | CaOV3 | ++ |
| | SKOV3 | ++ |
| | GB | ++ |
| Colon | SW48 | ++ |
| | SW480 | ++ |
| Breast | MD435 | ++ |
| | MD436 | ++ |
| Fibroblast | MRC-5 | − |
| Melanoma | A375 | ++ |
| Sarcoma | SK-UT-1 | + |
| Hematopoietic | K562 | − |
| | Daudi | − |
| | Jurkatt | − |

[1]Strong (++), moderate (+), weak (±), negative (−)

EXAMPLE VI

The relative reactivity of human anti-cervix surface reacting monoclonal antibody CR4E8E10E10 with cryostat tissue sections of squamous carcinoma cervix and other malignant or non-malignant tissues was carried out using the immunoperoxidase procedures of the invention. The resulting slides were scored using the procedures described (supra). The relative reactivity found for each tissue section is summarized in Table 10. In some cases, the results were not readable and were scored "unsatisfactory."

TABLE 10
Reactivity of Human Anti-Cervix Surface Reacting Monoclonal Antibody CR4E8E10E10 with Cryostat Sections of Squamous Carcinoma Cervix and other Malignant and Normal Tissues

| | No. of Patient Specimen | Relative Immunoreactivity[1] |
|---|---|---|
| Malignant Tissues | | |
| Cervix | 1 | ++ |
| Ovary | 5 | − − − − ± |
| Breast | 2 | ++ |
| Kidney | 1 | − |
| Lung | 1 | + |
| Colon | 1 | ++ |

TABLE 10-continued

Reactivity of Human Anti-Cervix Surface Reacting Monoclonal Antibody CR4E8E10E10 with Cryostat Sections of Squamous Carcinoma Cervix and other Malignant and Normal Tissues

| | No. of Patient Specimen | Relative Immunoreactivity[1] |
|---|---|---|
| Normal tissues | | |
| Cervix | 1 | unsatisfactory |
| Ovary | 2 | − − |
| Breast | 2 | + + + + |
| Kidney | 2 | − − |
| Lung | 2 | NS[2] − |
| Peritoneum | 1 | unsatisfactory |

[1]Strong (++), moderate (+), weak (±), negative (−)
[2]NS = nonspecific second antibody reaction

EXAMPLE VII

Figure 4A:
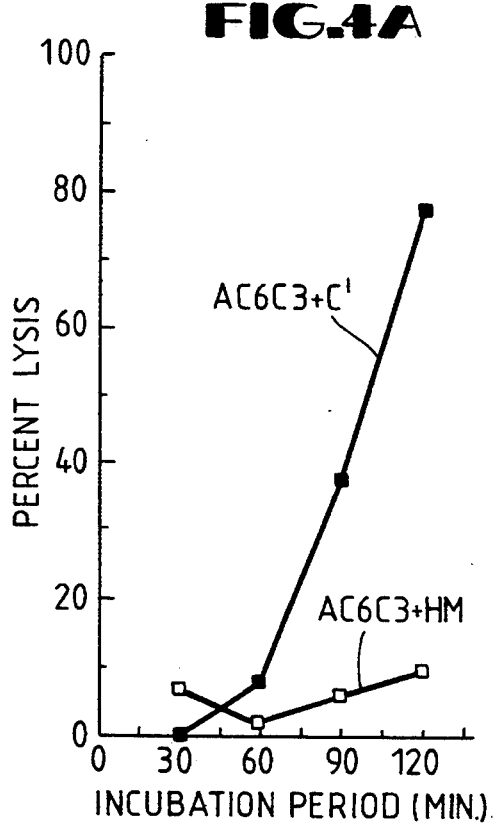
FIG. 4A. Complement Mediated Cytotoxicity of AC6C3. Per cent lysis of MD2774 ovarian tumor cells by AC6C3 with complement (C) and with hybridoma medium (HM).
Figure 4B:
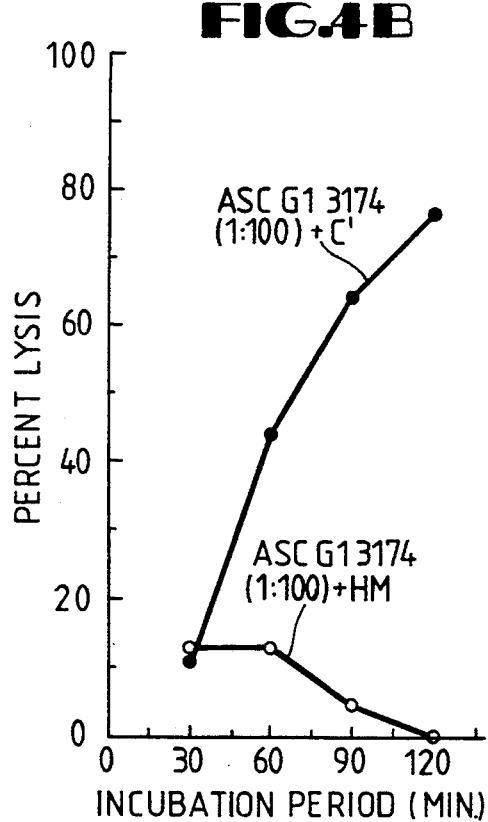
FIG. 4B. Complement Mediated Cytotoxicity of AC6C3. Per cent lysis of MD2774 ovarian tumor cells by ASC G1 3174 with complement and with hybridoma medium (HM). ASC G1 3174 is a mouse anti-MD2774 known to exhibit complement-dependent cytotoxicity against MD2774 cells.

Complement mediated cytotoxicity of the anti-ovarian monoclonal antibody derived from the AC6C3 hybridoma of the invention was carried out against MDAH 2774 cells as described supra. Positive control antibody known to exhibit complement mediated cytotoxicity against MDAH 2774 was included. The ability of AC6C3 monoclonal antibody to affect complement mediated cytotoxicity when compared to the positive control is shown in FIGS. 4(A) and (B).

EXAMPLE VIII

Immunoreactivity of the AC6C3 human monoclonal antibody

In order to characterize the immunoreactivity of the AC6C3 monoclonal antibody, saturation binding studies of AC6C3 on SKOV3 cells were performed as described by Ioannides et al. 1982 and Lindmo et al. 1984. SKOV3 cells were detached with EDTA. Cells were incubated with decreasing concentrations of unlabelled AC6C3 at 4° C. for 1 hour. AC6C3 was labeled with carrier free $^{125}$I (DuPont-NEN, Boston, Mass.) and specific activity 17.4 mCi/μg with 84% labeling efficiency. $^{125}$I-labeled AC6C3 was added to SKOV3 cells that had been preincubated with cold AC6C3 cells at concentrations ranging from 2.5 to 80 ng/ml and to control SKOV3 cells alone. Nonspecific binding in the presence of 100–500 fold excess antibody did not exceed 20% of binding in the absence of antibody. Scatchard plot analysis (Hudson and Hay 1976) and determination of the association constant ($K_A$) was accomplished using the STATVIEW 512 computer program.

Figure 5:
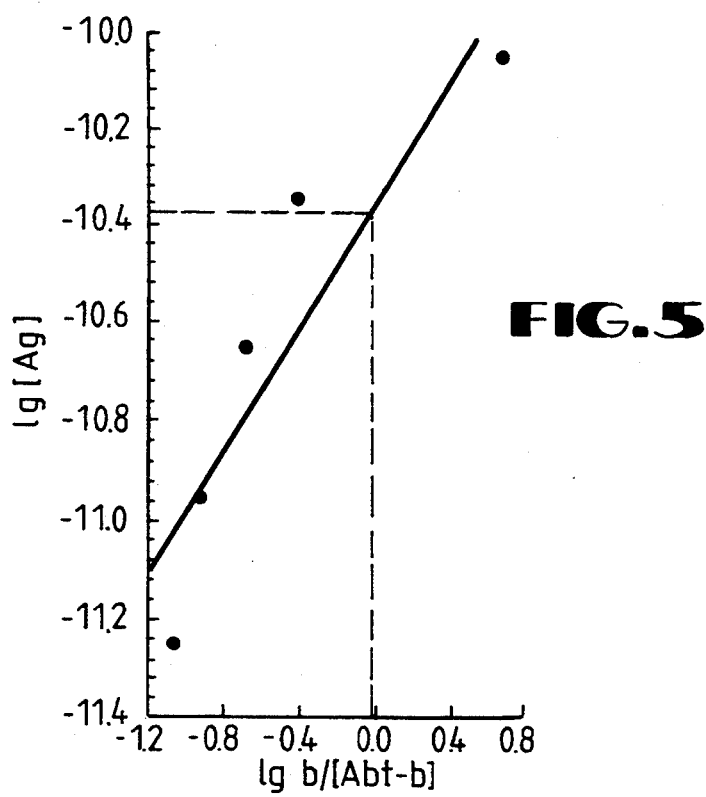
FIG. 5. Immunoreactivity of human MAb AC6C3 with SKOV3 cells. Lg[Ag]=log$_{10}$ concentration of AC6C3. b=concentration of bound AC6C3. [Abt]=total concentration of antibody combining sites.

Graphic representation of the saturation binding studies were plotted in Scatchard form (FIG. 5). The intercept on the "Y" (or $\log_{10}[Ag]$) axis equals $1/K_A$ when $\log_{10} b/[Abt-b] = 0$. The $K_A$ value was determined to be within the range $2.0$–$3.0 \times 10^{10}$ M$^{-1}$.

EXAMPLE IX

Determination of the components recognized by AC6C3

In order to determine the specific binding sites for AC6C3 found on the cell surface of tumor cells, protein blots of SDS-PAGE were generated and immunoprecipitations were accomplished. The applicants were able to detect the presence of specific molecules on the cell-surface of a tumor cell which bound the monoclonal antibody.

Figures 6A, 6B:
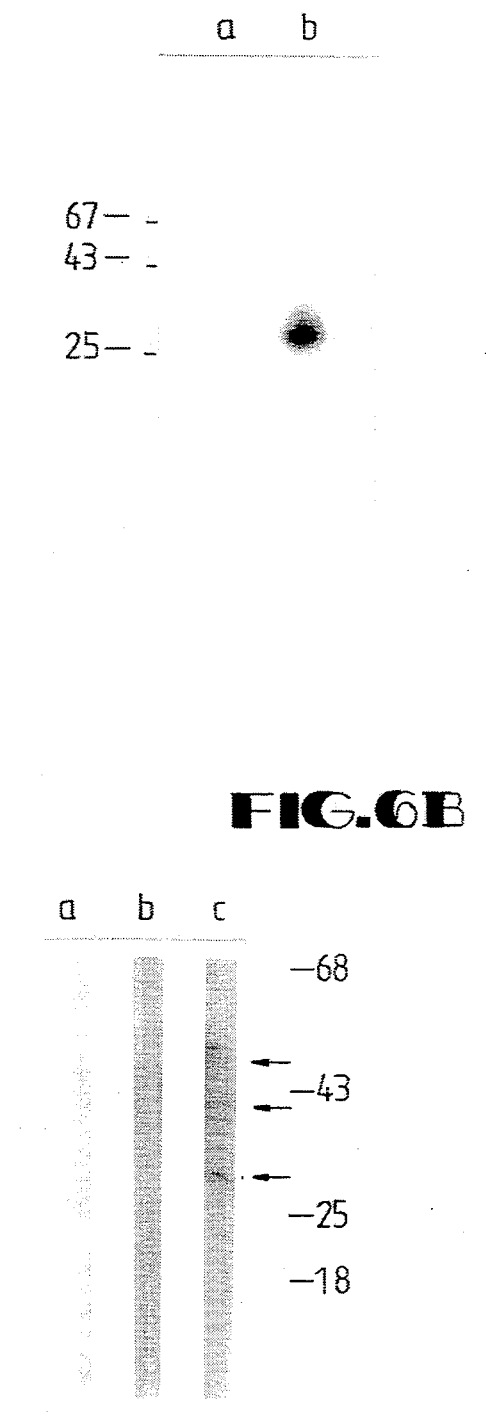

Western blotting was performed as described by Ioannides et al., 1987. SKOV3 cells were detached with EDTA, washed and lysed with 0.5% NP40 in PBS containing protease inhibitors. Lysates were electrophoresed by 8–10% SDS-PAGE and then transferred onto nitrocellulose paper strips (Ioannides et al. 1987, Ioannides et al. 1989). The strips were incubated with AC6C3 or an irrelevant human MAb H1 followed by staining with a conjugated peroxidase antihuman IgM (TAGO) and a peroxidase substrate consisting of 0.3% 4-chloronapthol in methanol containing 0.02% $H_2O_2$ (Sigma, St. Louis, Mo.). Molecular weight markers used in the immunopreciptiation experiments were: bovine serum albumin (67–68 Kd); ovalbumin (43 Kd); carbonic anhydrase (25–29 Kd). The relative positions of these markers are shown in FIG. 6A. Molecular weight markers used in the Western Blotting experiments were: bovine serum albumin (67–68 Kd); ovalbumin (43 Kd); carbonic anhydrase (25–29 Kd); and beta lactoglobulin (18 Kd). The relative positions of these markers are shown in FIG. 6B.

Immunoprecipitation of cell surface antigens was performed as previously described (Ioannides et al. 1987). SKOV3 cells were labelled with carrier free $^{125}$I (Amersham, Arlington Heights, Ill.), specific activity 14.3 mCi/μg. $^{125}$I labeled SKOV3 cells were lysed as above and reacted with AC6C3 or an irrelevant human MAb H1 coupled to Sepharose beads (Pharmacia, Piscataway, N.J.). The gels were dried and the position of the bands were determined by autoradiography utilizing KODAK-X-R51 film. Positions of the bands were compared with the migration of the prestained molecular weight markers above (Bethesda Research Laboratories, Bethesda, Md.).

Immunoprecipitation with the AC6C3MAb identified a 32 Kd band expressed on the surface of SKOV3 cells. FIG. 6A is representative of two separate experiments. Two additional bands at 40 Kd and 52 Kd were detected on lysates of the SKOV3 cell line by Western blotting. FIG. 6B is representative of 3 experiments.

Thus, both immunoprecipitation and Western blotting identified a 32 Kd band that appeared to be expressed on the cell surface of SKOV3 cells. Furthermore, by Western blotting two additional bands either in single or duplex form, were identified at 40 and at 52 Kd. The 40 and 52 Kd bands were not detected by immunoprecipitation, suggesting that they are not expressed on the cell surface, whereas the same epitope recognized extracellularly by AC6C3 MAb may also be present on intracellular proteins. Whether the epitope is present on the same or on different proteins is yet to be determined.

REFERENCES

Al-Azzawi, et al., *J. Clin. Lab. Immunl.* 22:71–75 (1987).

Aotsuka and Hagiwara, *Eur. J. Cancer Clin. Oncol.* 24:829–838 (1988).

Boulianne, et al., *Nature* 312:643–646 (1984).

Cote, et al., *Proc. Natl. Acad. Sci. USA* 83:2959–2963 (1986).

Freedman, et al., *In Vitro* 18:719–726 (1982).

Freedman, et al., *Gynecologic Oncol.* 29:337–347 (1988a).

Freedman, et al., AACR (abstract) (1988b).

Freedman, et al., *Am. J. Clin. Oncol.* (CCT) 12:244–250 (1989).

Glassy, et al., *Cancer Investigation* 5:449–457 (1987).

Glassy and Surh, U.S. Pat. No. 4,761,377 (1988).

Hagiwara and Sato, *Mol. Biol. Med.* 1:245–252 (1983).

Hanna, et al., *Cancer Res.* 45:3951–3961 (1985).

Handley, et al., PCT/U.S. Pat. No. 83/00781 (1983).

Handley, et al., U.S. Pat. No. 4,618,377 (1986).
Houghton, et al., *Proc. Natl. Acad. Sci. U.S.A.* 82:1242–1246 (1985).
Hudson and Hay, In: Practical Immunology, Blackwell Scientific Publications, pp. 93–99 (1976).
Ioannides, et al., *Int. J. Cancer* 29:147–152 (1982).
Ioannides, et al., *Proc. Natl. Acad. Sci. USA* 84:4244–4248 (1987).
Ioannides, et al., *Anti-cancer Res.* 9:81–96 (1989).
Koprowska, et al., *Acta Cytologia* 30:207–213 (1986).
Lindmo, et al., *J. Immunol. Meth.* 72:77–89 (1984).
Lotzova, et al., U.S. patent application No. 336,045 (1989).
Morrison, et al., *Proc. Natl. Acad. Sci. USA* 81:6851–6858 (1984).
Neuberger, et al., *Nature* 312:604–608 (1984).
Oldham, et al., *J. Clin. Oncol.* 2:1235–1244 (1984).
Sears, et al., *Lancet* 1:762–765 (1982).
Smith, et al., *J. Immunol. Meth.* 105:263–273 (1987).
Wallack, et al., *J. Biol. Response Modif.* 2:586≅596 (1983).

We claim:

1. The human monoclonal antibody produced by the hybridoma with ATCC accession number HB 10305.

2. The hybridoma cell line with ATCC accession number HB 10305.